(12) United States Patent
Edgerton et al.

(10) Patent No.: US 10,751,533 B2
(45) Date of Patent: Aug. 25, 2020

(54) REGULATION OF AUTONOMIC CONTROL OF BLADDER VOIDING AFTER A COMPLETE SPINAL CORD INJURY

(71) Applicant: The Regents of the University of California, Oakland, CA (US)

(72) Inventors: Victor Reggie Edgerton, Los Angeles, CA (US); Parag Gad, Woodland Hills, CA (US); Roland R. Roy, Playa Vista, CA (US); Yury P. Gerasimenko, Los Angeles, CA (US); Daniel C. Lu, Los Angeles, CA (US); Hui Zhong, Monterey Park, CA (US)

(73) Assignee: The Regents of the University of California, Oakland, CA (US)

( * ) Notice: Subject to any disclaimer, the term of this patent is extended or adjusted under 35 U.S.C. 154(b) by 176 days.

(21) Appl. No.: 15/505,053

(22) PCT Filed: Aug. 21, 2015

(86) PCT No.: PCT/US2015/046378
§ 371 (c)(1),
(2) Date: Feb. 17, 2017

(87) PCT Pub. No.: WO2016/029159
PCT Pub. Date: Feb. 25, 2016

(65) Prior Publication Data
US 2017/0274209 A1 Sep. 28, 2017

Related U.S. Application Data

(60) Provisional application No. 62/040,334, filed on Aug. 21, 2014.

(51) Int. Cl.
*A61N 1/36* (2006.01)
*A61K 31/506* (2006.01)
(Continued)

(52) U.S. Cl.
CPC .......... *A61N 1/36007* (2013.01); *A61H 3/00* (2013.01); *A61K 31/475* (2013.01);
(Continued)

(58) Field of Classification Search
USPC .......................................................... 607/3
See application file for complete search history.

(56) References Cited

U.S. PATENT DOCUMENTS 3,543,761 A 12/1970 Bradley
3,662,758 A 5/1972 Glover
(Continued)

FOREIGN PATENT DOCUMENTS

AU 2012204526 A1 7/2013
CA 2 823 592 A1 7/2012
(Continued)

OTHER PUBLICATIONS

U.S. Office Action dated Apr. 8, 2015 issued in U.S. Appl. No. 14/355,812.
(Continued)

*Primary Examiner* — Nicole F Lavert
(74) *Attorney, Agent, or Firm* — Tom Hunter; Weaver Austin Villeneuve & Sampson LLP

(57) ABSTRACT

In various embodiments methods and devices are provided for regulating bladder function in a subject after a spinal cord and/or brain injury. In certain embodiments the methods comprise applying a pattern of electrical stimulation to the Lumbosacral spinal cord at a frequency and intensity sufficient to initiate micturition and/or to improve the amount of bladder emptying. In certain embodiments the electrical stimulation is at a frequency and intensity sufficient to improve the amount of bladder emptying (e.g., to provide at least 30% emptying or at least 40% emptying, or at least 50% emptying, or at least 60% emptying, or at least (Continued)

70% emptying, or at least 80% emptying, or at least 90% emptying, or at least 95% emptying.

26 Claims, 14 Drawing Sheets

(51) Int. Cl.
  *A61K 45/06* (2006.01)
  *A61H 3/00* (2006.01)
  *A61K 31/475* (2006.01)
  *A61K 31/496* (2006.01)
  *A63B 21/06* (2006.01)
  *A63B 22/02* (2006.01)

(52) U.S. Cl.
  CPC .......... *A61K 31/496* (2013.01); *A61K 31/506* (2013.01); *A61K 45/06* (2013.01); *A61N 1/3606* (2013.01); *A61N 1/36014* (2013.01); *A61N 1/36071* (2013.01); *A63B 21/06* (2013.01); *A63B 22/02* (2013.01); *A61N 1/36157* (2013.01); *A61N 1/36171* (2013.01); *A61N 1/36175* (2013.01)

(56) References Cited

U.S. PATENT DOCUMENTS

| | | |
|---|---|---|
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,559,948 A | 12/1985 | Liss et al. |
| 4,573,481 A | 3/1986 | Bullara et al. |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel et al. |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,381,192 B2 | 6/2008 | Brodard et al. |
| 7,415,309 B2 | 8/2008 | Mcintyre |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen et al. |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt et al. |
| 8,155,750 B2 | 4/2012 | Jaax et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,332,029 B2 | 12/2012 | Glukhovsky et al. |
| 8,346,366 B2 | 1/2013 | Arle et al. |
| 8,352,036 B2 | 1/2013 | DiMarco et al. |

(56) References Cited

U.S. PATENT DOCUMENTS

| | | |
|---|---|---|
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,588,884 B2 | 11/2013 | Hegde et al. |
| 8,700,145 B2 | 4/2014 | Kilgard et al. |
| 8,712,546 B2 | 4/2014 | Kim et al. |
| 8,750,957 B2 | 6/2014 | Tang et al. |
| 8,805,542 B2 | 8/2014 | Tai et al. |
| 9,072,891 B1 | 7/2015 | Rao |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,272,143 B2 | 3/2016 | Libbus et al. |
| 9,283,391 B2 | 3/2016 | Ahmed |
| 9,393,409 B2 | 7/2016 | Edgerton et al. |
| 9,415,218 B2 | 8/2016 | Edgerton et al. |
| 9,610,442 B2 | 4/2017 | Yoo et al. |
| 9,993,642 B2 | 6/2018 | Gerasimenko et al. |
| 10,137,299 B2 | 11/2018 | Lu et al. |
| 2002/0055779 A1 | 5/2002 | Andrews |
| 2002/0111661 A1 | 8/2002 | Cross et al. |
| 2002/0115945 A1 | 8/2002 | Herman et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0100933 A1 | 5/2003 | Ayal et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald et al. |
| 2004/0133248 A1 | 7/2004 | Frei et al. |
| 2004/0138518 A1 | 7/2004 | Rise et al. |
| 2005/0004622 A1 | 1/2005 | Cullen et al. |
| 2005/0070982 A1 | 3/2005 | Heruth et al. |
| 2005/0075669 A1 | 4/2005 | King |
| 2005/0075678 A1 | 4/2005 | Faul |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0246004 A1 | 11/2005 | Cameron et al. |
| 2005/0278000 A1 | 12/2005 | Strother et al. |
| 2006/0003090 A1 | 1/2006 | Rodger et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0239482 A1 | 10/2006 | Hatoum |
| 2007/0016097 A1 | 1/2007 | Farquhar et al. |
| 2007/0016266 A1 | 1/2007 | Paul, Jr. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0073357 A1 | 3/2007 | Rooney et al. |
| 2007/0083240 A1 | 4/2007 | Peterson et al. |
| 2007/0156179 A1 | 7/2007 | Karashurov |
| 2007/0168008 A1 | 7/2007 | Olsen |
| 2007/0179534 A1 | 8/2007 | Firlik et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2008/0021513 A1 | 1/2008 | Thacker et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0103579 A1 | 5/2008 | Gerber |
| 2008/0140152 A1 | 6/2008 | Imran et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0215113 A1 | 9/2008 | Pawlowicz |
| 2008/0221653 A1 | 9/2008 | Agrawal et al. |
| 2008/0228241 A1 | 9/2008 | Sachs |
| 2008/0228250 A1 | 9/2008 | Mironer |
| 2008/0234791 A1 | 9/2008 | Arle et al. |
| 2008/0279896 A1 | 11/2008 | Heinen et al. |
| 2009/0012436 A1 | 1/2009 | Lanfermann et al. |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0270960 A1 | 10/2009 | Zhao et al. |
| 2009/0281599 A1 | 11/2009 | Thacker et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0042193 A1 | 2/2010 | Slavin |
| 2010/0070007 A1 | 3/2010 | Parker et al. |
| 2010/0114239 A1 | 5/2010 | McDonald et al. |
| 2010/0125313 A1 | 5/2010 | Lee et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0305660 A1 | 12/2010 | Hegi et al. |
| 2010/0318168 A1 | 12/2010 | Bighetti |
| 2010/0331925 A1 | 12/2010 | Peterson |
| 2011/0029040 A1 | 2/2011 | Walker et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054579 A1 | 3/2011 | Kumar et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184488 A1 | 7/2011 | De Ridder |
| 2011/0184489 A1 | 7/2011 | Nicolelis et al. |
| 2011/0218594 A1 | 9/2011 | Doran et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230701 A1 | 9/2011 | Simon et al. |
| 2011/0245734 A1 | 10/2011 | Wagner et al. |
| 2011/0276107 A1 | 11/2011 | Simon et al. |

(56) References Cited

U.S. PATENT DOCUMENTS

| | | |
|---|---|---|
| 2011/0288609 A1 | 11/2011 | Tehrani et al. |
| 2011/0295100 A1 | 12/2011 | Rolston et al. |
| 2012/0006793 A1 | 1/2012 | Swanson |
| 2012/0029528 A1 | 2/2012 | Macdonald et al. |
| 2012/0035684 A1 | 2/2012 | Thompson et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0123293 A1 | 5/2012 | Shah et al. |
| 2012/0126392 A1 | 5/2012 | Kalvesten et al. |
| 2012/0165899 A1 | 6/2012 | Gliner |
| 2012/0172946 A1 | 7/2012 | Altaris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0221073 A1 | 8/2012 | Southwell et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330391 A1 | 12/2012 | Bradley et al. |
| 2013/0013041 A1 | 1/2013 | Glukhovsky et al. |
| 2013/0030319 A1 | 1/2013 | Hettrick et al. |
| 2013/0030501 A1 | 1/2013 | Feler et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0110196 A1 | 5/2013 | Alataris et al. |
| 2013/0123568 A1 | 5/2013 | Hamilton et al. |
| 2013/0123659 A1 | 5/2013 | Bartol et al. |
| 2013/0165991 A1 | 6/2013 | Kim et al. |
| 2013/0197408 A1 | 8/2013 | Goldfarb et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1* | 10/2013 | Stone ............... A61N 1/3606 600/586 |
| 2013/0303873 A1 | 11/2013 | Voros et al. |
| 2013/0304159 A1 | 11/2013 | Simon et al. |
| 2013/0310911 A1 | 11/2013 | Tai et al. |
| 2014/0031893 A1 | 1/2014 | Walker et al. |
| 2014/0046407 A1 | 2/2014 | Ben-Ezra et al. |
| 2014/0058490 A1 | 2/2014 | DiMarco |
| 2014/0066950 A1 | 3/2014 | Macdonald et al. |
| 2014/0067007 A1 | 3/2014 | Drees et al. |
| 2014/0067354 A1 | 3/2014 | Kaula et al. |
| 2014/0081071 A1 | 3/2014 | Simon et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0180361 A1 | 6/2014 | Burdick et al. |
| 2014/0213842 A1 | 7/2014 | Simon et al. |
| 2014/0236257 A1 | 8/2014 | Parker et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0357936 A1 | 12/2014 | Simon et al. |
| 2015/0065559 A1 | 3/2015 | Feinstein et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0231396 A1 | 8/2015 | Burdick et al. |
| 2015/0265830 A1 | 9/2015 | Simon et al. |
| 2016/0030737 A1 | 2/2016 | Gerasimenko et al. |
| 2016/0030748 A1 | 2/2016 | Edgerton et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0339239 A1 | 11/2016 | Yoo et al. |
| 2017/0007831 A1 | 1/2017 | Edgerton et al. |
| 2017/0157389 A1 | 6/2017 | Tai et al. |
| 2017/0165497 A1 | 6/2017 | Lu |
| 2017/0246450 A1 | 8/2017 | Liu et al. |
| 2017/0246452 A1 | 8/2017 | Liu et al. |
| 2017/0296837 A1 | 10/2017 | Jin |
| 2018/0185642 A1 | 7/2018 | Lu |
| 2018/0256906 A1 | 9/2018 | Piyonka et al. |
| 2018/0280693 A1 | 10/2018 | Edgerton et al. |
| 2018/0361146 A1 | 12/2018 | Gerasimenko et al. |
| 2019/0022371 A1 | 1/2019 | Chang et al. |
| 2019/0167987 A1 | 6/2019 | Lu et al. |
| 2019/0381313 A1 | 12/2019 | Lu |

FOREIGN PATENT DOCUMENTS

| | | |
|---|---|---|
| EP | 2661307 A2 | 11/2013 |
| EP | 2968940 A1 | 1/2016 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | WO 97/047357 A1 | 12/1997 |
| WO | WO 03/026735 A2 | 4/2003 |
| WO | WO 03/092795 A1 | 11/2003 |
| WO | WO 2004/087116 A2 | 10/2004 |
| WO | WO 2005/051306 A2 | 6/2005 |
| WO | WO 2005/087307 A2 | 9/2005 |
| WO | WO 2007/007058 A1 | 1/2007 |
| WO | WO 2007/107831 A2 | 9/2007 |
| WO | WO 2008/109862 A1 | 9/2008 |
| WO | WO 2008/121891 A1 | 10/2008 |
| WO | WO 2009/042217 A1 | 4/2009 |
| WO | WO 2009/111142 A2 | 9/2009 |
| WO | WO 2010/055421 A1 | 5/2010 |
| WO | WO 2010/114998 A1 | 10/2010 |
| WO | WO 2010/124128 A1 | 10/2010 |
| WO | WO 2012/094346 A2 | 7/2012 |
| WO | WO 2012/100260 A2 | 7/2012 |
| WO | WO 2012/129574 A2 | 9/2012 |
| WO | WO 2013/071307 A1 | 5/2013 |
| WO | WO 2013/071309 A1 | 5/2013 |
| WO | WO 2014/144785 A1 | 9/2014 |
| WO | WO 2015/048563 A2 | 4/2015 |
| WO | WO 2016/029159 A2 | 2/2016 |
| WO | WO 2016/033369 A1 | 3/2016 |
| WO | WO 2016/033372 A1 | 3/2016 |
| WO | WO 2017/011410 A1 | 1/2017 |
| WO | WO 2017/024276 A1 | 2/2017 |
| WO | WO 2017/035512 A1 | 3/2017 |
| WO | WO 2017/044904 A1 | 3/2017 |
| WO | WO 2018/140531 A1 | 8/2018 |

(56) References Cited

FOREIGN PATENT DOCUMENTS

| WO | WO 2018/217791 A1 | 11/2018 |
|---|---|---|
| WO | WO 2020/041502 A1 | 2/2020 |
| WO | WO 2020/041633 A1 | 2/2020 |

OTHER PUBLICATIONS

U.S. Final Office Action dated Sep. 21, 2015 issued in U.S. Appl. No. 14/355,812.
U.S. Notice of Allowance dated Apr. 13, 2016 issued in U.S. Appl. No. 14/355,812.
U.S. Office Action dated Oct. 18, 2016 issued in U.S. Appl. No. 15/208,529.
U.S. Final Office Action dated Jul. 13, 2017 issued in U.S. Appl. No. 15/208,529.
U.S. Office Action dated Jul. 27, 2018 issued in U.S. Appl. No. 15/208,529.
U.S. Office Action dated Oct. 3, 2017 issued in U.S. Appl. No. 15/025,201.
U.S. Notice of Allowance dated Aug. 1, 2018 issued in U.S. Appl. No. 15/025,201.
U.S. Office Action dated Jul. 13, 2016 issued in U.S. Appl. No. 14/775,618.
U.S. Final Office Action dated Apr. 25, 2017 issued in U.S. Appl. No. 14/775,618.
U.S. Notice of Allowance dated Jan. 18, 2018 issued in U.S. Appl. No. 14/775,618.
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878.
PCT International Preliminary Report on Patentability dated May 22, 2014 issued in PCT/US2012/064878.
Australian Patent Examination Report No. 1 dated Jul. 11, 2016 issued in AU 2012334926.
Canadian Office Action dated Aug. 31, 2018 issued in CA 2,864,473.
European Communication pursuant to Rule 114(2) EPC regarding observations by a third party dated Mar. 27, 2015 issued in EP 12 847 885.6.
European Extended Search Report dated May 6, 2015 issued in EP 12 847 885.6.
European Office Action dated Apr. 15, 2016 issued in EP 12 847 885.6.
European Reply to Communication of Apr. 15, 2016 dated Oct. 24, 2016 in EP 12 847 885.6.
European Second Office Action dated Feb. 16, 2017 issued in EP 12 847 885.6.
PCT Declaration of Non-Establishment of International Search Report and Written Opinion dated Dec. 24, 2014 issued in PCT/US2014/057886.
PCT International Preliminary Report on Patentability and Written Opinion dated Apr. 7, 2016 issued in PCT/US2014/057886.
Australian Examination report No. 1 dated Jan. 11, 2019 issued in AU 2014324660.
European Extended Search Report dated May 10, 2017 issued in EP 14849355.4.
European Office Action dated Jul. 20, 2018 issued in EP 14849355.4.
PCT International Search Report and Written Opinion dated Aug. 6, 2014 issued in PCT/US2014/029340.
PCT International Preliminary Report on Patentability dated Sep. 24, 2015 issued in PCT/US2014/029340.
Australian Patent Examination Report No. 1 dated May 11, 2018 issued in AU 2014228794.
European Extended Search Report dated Nov. 8, 2016 issued in EP 14 76 5477.6.
European Office Action dated Nov. 14, 2018 issued in EP 14 76 5477.6.
PCT International Search Report and Written Opinion dated Dec. 5, 2016 issued in PCT/US2016/045898.
PCT International Preliminary Report on Patentability and Written Opinion dated Feb. 15, 2018 issued in PCT/US2016/045898.
European Extended Search Report dated Dec. 13, 2018 issued in EP 16833973.7.
PCT International Search Report and Written Opinion dated Dec. 8, 2015 issued in PCT/US2015/047268.
PCT International Preliminary Report on Patentability and Written Opinion dated Feb. 28, 2017 issued in PCT/US2015/047268.
European Extended Search Report dated Mar. 1, 2018 issued in EP 15836927.2.
PCT International Search Report and Written Opinion dated Dec. 3, 2015 issued in PCT/US2015/047272.
PCT International Preliminary Report on Patentability and Written Opinion dated Feb. 28, 2017 issued in PCT/US2015/047272.
PCT Declaration of Non-Establishment of International Search Report and Written Opinion dated Dec. 1, 2015 issued in PCT/US2015/046378.
PCT International Preliminary Report on Patentability and Written Opinion dated Feb. 21, 2017 issued in PCT/US2015/046378.
European Extended Search Report dated Apr. 4, 2018 issued in EP 15834593.4.
PCT International Search Report and Written Opinion dated Sep. 12, 2016 issued in PCT/US2016/041802.
PCT International Preliminary Report on Patentability and Written Opinion dated Jan. 25, 2018 issued in PCT/US2016/041802.
European Extended Search Report dated Feb. 19, 2019 issued in EP 16825005.8.
PCT International Search Report and Written Opinion dated Dec. 5, 2016 issued in PCT/US2016/049129.
PCT International Preliminary Report on Patentability and Written Opinion dated Mar. 8, 2018 issued in PCT/US2016/049129.
PCT International Search Report and Written Opinion dated Mar. 12, 2018 issued in PCT/US2018/015098.
PCT International Search Report and Written Opinion dated Aug. 31, 2018 issued in PCT/US2018/033942.
PCT International Search Report dated Mar. 19, 2013 issued in PCT/US2012/064874.
PCT International Search Report dated Mar. 19, 2013 issued in PCT/US2012/064878.
PCT International Search Report dated Sep. 3, 2012 issued in PCT/US2012/022257.
PCT International Search Report dated Oct. 31, 2012 issued in PCT/US2012/030624.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and running in humans," *J Physiol.* 582.3:1125-1139.
Danner S.M., Hofstoetter U.S., Ladenbauer J., Rattay F., and Minassian K. (Mar. 2011) "Can the human lumbar posterior columns be stimulated by transcutaneous spinal cord stimulation? A modeling study" *Europe PMC Funders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology*, 74:173-176.
Edgerton and Harkema (2011) "Epidural stimulation of the spinal cord in spinal cord injury: current status and future challenges" *Expert Rev Neurother.* 11(10): 1351-1353. doi:10.1586/ern.11.129 [NIH Public Access—Author Manuscript—5 pages].
Fong et al. (2009) "Recovery of control of posture and locomotion after a spinal cord injury: solutions staring us in the face," *Progress in Brain Research*, Elsevier Amsterdam, NL,175:393-418.

(56) References Cited

OTHER PUBLICATIONS

Ganley et al., (2005) "Epidural Spinal Cord Stimulation Improves Locomoter Performance in Low ASIA C, Wheelchair-Dependent, Spinal Cord-Injured Individuals: Insights from Metabolic Response," *Top. Spinal Cord Inj. Rehabil*;11(2):50-63.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol.* 98:2525-2536.
Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages. [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," *Spinal Cord.* 40:65-68.
Hofstoetter, U.S. et al. (Aug. 2008) "Modification of Reflex Responses to Lumbar Posterior Root Stimulation by Motor Tasks in Healthy Subjects," *Artif Organs*, 32(8):644-648.
Ichiyama et al. (2005) "Hindlimb stepping movements in complete spinal rats induced by epidural spinal cord stimulation" *Neuroscience Letters*, 383:339-344.
Kitano K., Koceja D.M. (2009) "Spinal reflex in human lower leg muscles evoked by transcutaneous spinal cord stimulation," *J Neurosci Methods.* 180:111-115.
Minasian et al. (2010) "Transcutaneous stimulation of the human lumbar spinal cord: Facilitating locomotor output in spinal cord injury," *Conf. Proceedings Soc. for Neurosci.*, Abstract No. 286.19, 1 page.
Minassian et al. (Aug. 2011) "Transcutaneous spinal cord stimulation," *International Society for Restorative Neurology*, http://restorativeneurology.org/resource-center/assessments/transcutaneous-lumbar-spinal-cord-stimulation/; http://restorativeneurology.org/wp-content/uploads/2011/08/Transcutaneous-spinal-cord-stimulation_long.pdf, 6 pp.
Minassian et al. (Mar. 2007) "Posterior root-muscle reflexes elicited by transcutaneous stimulation of the human lumbosacral cord," *Muscle & Nerve* 35:327-336.
Nandra et al., (2014) "Microelectrode Implants for Spinal Cord Stimulation in Rats," *Thesis, California Institute of Technology*, Pasadena, California, Defended on Sep. 24, 2014, 104 pages.
Nandra et al., (Jan. 23, 2011) "A Parylene-Based Microelectrode Arrary Implant for Spinal Cord Stimulation in Rats," *Conf. Proc. IEEE Eng. Med. Biol. Soc.*, pp. 1007-1010.
Rodger et al., (2007) "High Density Flexible Parylene-Based Multielectrode Arrays for Retinal and Spinal Cord Stimulation," Transducers & Eurosensors, Proc. of the 14th International Conference on Solid-State Sensors, Actuators and Microsystems, Lyon, France, Jun. 10-14, 2007, *IEEE*, pp. 1385-1388.
Seifert et al. (Nov. 1, 2002) "Restoration of Movement Using Functional Electrical Stimulation and Bayes' Theorem," *The Journal of Neuroscience*, 22(1):9465-9474.
Tanabe et al. (2008) "Effects of transcutaneous electrical stimulation combined with locomotion-like movement in the treatment of post-stroke gait disorder: a single-case study," 30(5):411-416 abstract, 1 page.
Ward, Alex R. (Feb. 2009) "Electrical Stimulation Using Kilohertz-Frequency Alternating Current ," (2009) *Phys Ther*.89(2):181-190 [published online Dec. 18, 2008].

U.S. Final Office Action dated Apr. 19, 2019 issued in U.S. Appl. No. 15/208,529.
U.S. Office Action dated Oct. 28, 2019 issued in U.S. Appl. No. 15/208,529.
U.S. Office Action dated Oct. 31, 2019 issued in U.S. Appl. No. 15/750,499.
U.S. Office Action dated Jul. 22, 2019 issued in U.S. Appl. No. 15/506,696.
U.S. Office Action dated Apr. 17, 2019 issued in U.S. Appl. No. 15/344,381.
Canadian Office Action dated Jul. 30, 2019 issued in CA 2,864,473.
Australian Examination report No. 2 dated Nov. 7, 2019 issued in AU 2014324660.
European Office Action dated Sep. 27, 2019 issued in EP 14765477.6.
Australian Patent Examination Report No. 1 dated Jul. 18, 2019 issued in AU 2015308779.
Australian Patent Examination Report No. 1 dated Jun. 14, 2019 issued in AU 2015305237.
European Office Action dated Jul. 17, 2019 issued in EP 15834593.4.
PCT International Preliminary Report on Patentability and Written Opinion dated Jul. 30, 2019 issued in PCT/US2018/015098.
Andersson, et al., (2003) "CNS Involvement in Overactive Bladder." *Drugs*, 63(23): 2595-2611.
U.S. Office Action dated Apr. 10, 2020 issued in U.S. Appl. No. 16/200,467.
U.S. Office Action dated Jan. 8, 2020 issued in U.S. Appl. No. 15/975,678.
U.S. Notice of Allowance dated May 4, 2020 issued in U.S. Appl. No. 15/506,696.
U.S. Office Action dated Apr. 7, 2020 issued in U.S. Appl. No. 15/740,323.
U.S. Final Office Action dated Dec. 30, 2019 issued in U.S. Appl. No. 15/344,381.
Australian Examination report No. 3 dated Jan. 6, 2020 issued in AU 2014324660.
Australian Patent Examination Report No. 1 dated Jan. 6, 2020 issued in AU 2019206059.
European Extended Search Report dated Apr. 21, 2020 issued in EP 19201998.2.
Australian Patent Examination Report No. 2 dated Apr. 17, 2020 issued in AU 2015305237.
PCT International Preliminary Report on Patentability and Written Opinion dated Nov. 26, 2019 issued in PCT/US2018/033942.
PCT International Search Report and Written Opinion dated Nov. 14, 2019 issued in PCT/US2019/047777.
PCT International Search Report and Written Opinion dated Nov. 21, 2019 issued in PCT/US2019/047551.
Drummond, et al. (1996) "Thoracic impedance used for measuring chest wall movement in postoperative patients," *British Journal of Anaesthesia*, 77: 327-332.
Hovey, et al. (2006) "The Guide to Magnetic Stimulation," *The Magstim Company Ltd*, 45 pages.
Kapetanakis, et al. (2017) "Cauda Equina Syndrome Due to Lumbar Disc Herniation: a Review of Literature," *Folia Medial*, 59(4): 377-86.
Kondo, et al. (1997) "Laser monitoring of chest wall displacement," *Eur Respir J.*, 10: 1865-1869.
Niu et al., (2018) "A Proof-of-Concept Study of Transcutaneous Magnetic Spinal Cord Stimulation for Neurogenic Bladder," *Scientific Reports*, 8: 12549 (12 pages).
Wang, et al. (2017) "Incidence of C5 nerve root palsy after cervical surgery," *Medicine*, 96(45), 14 pages.

* cited by examiner

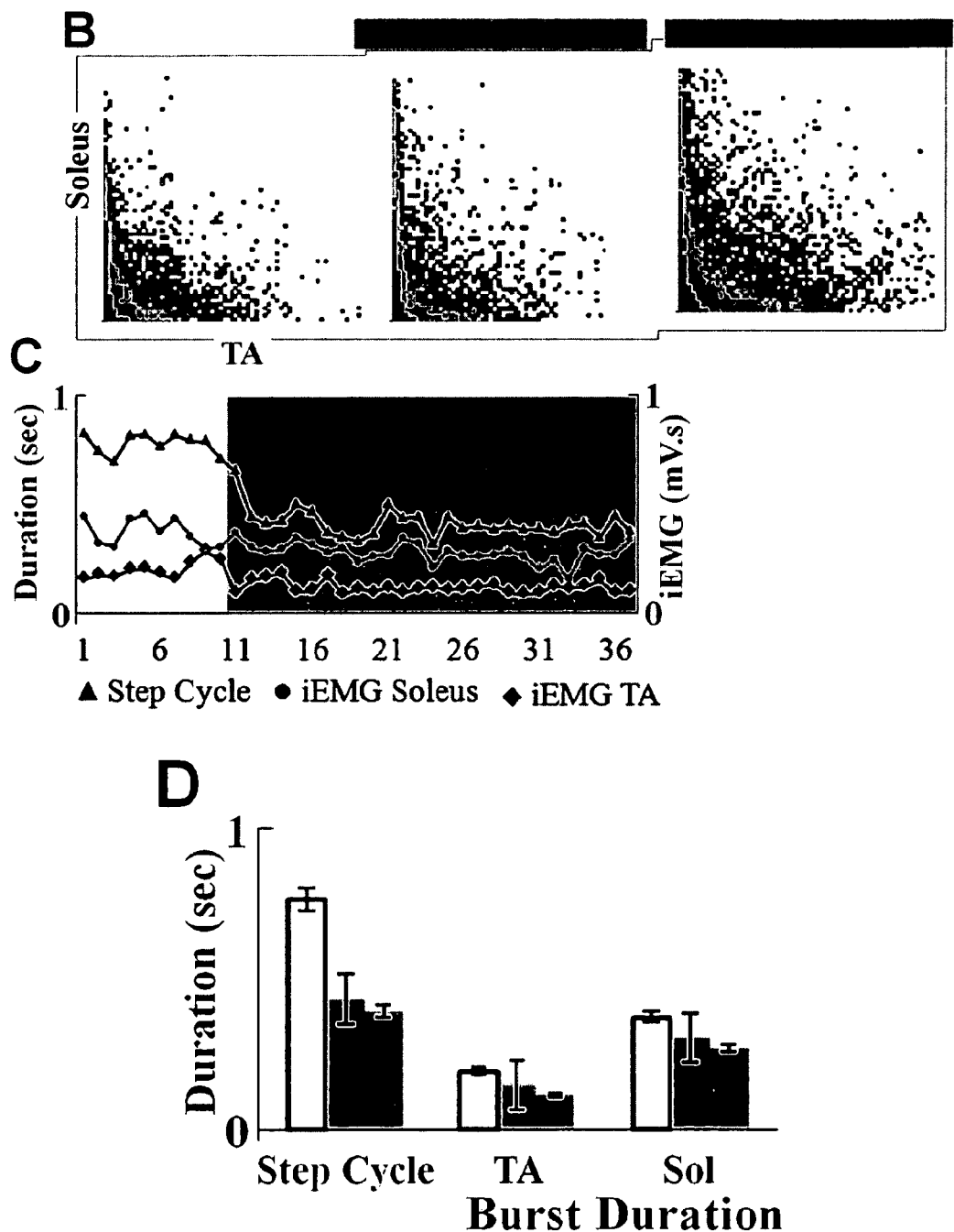
Fig. 1, cont'd.

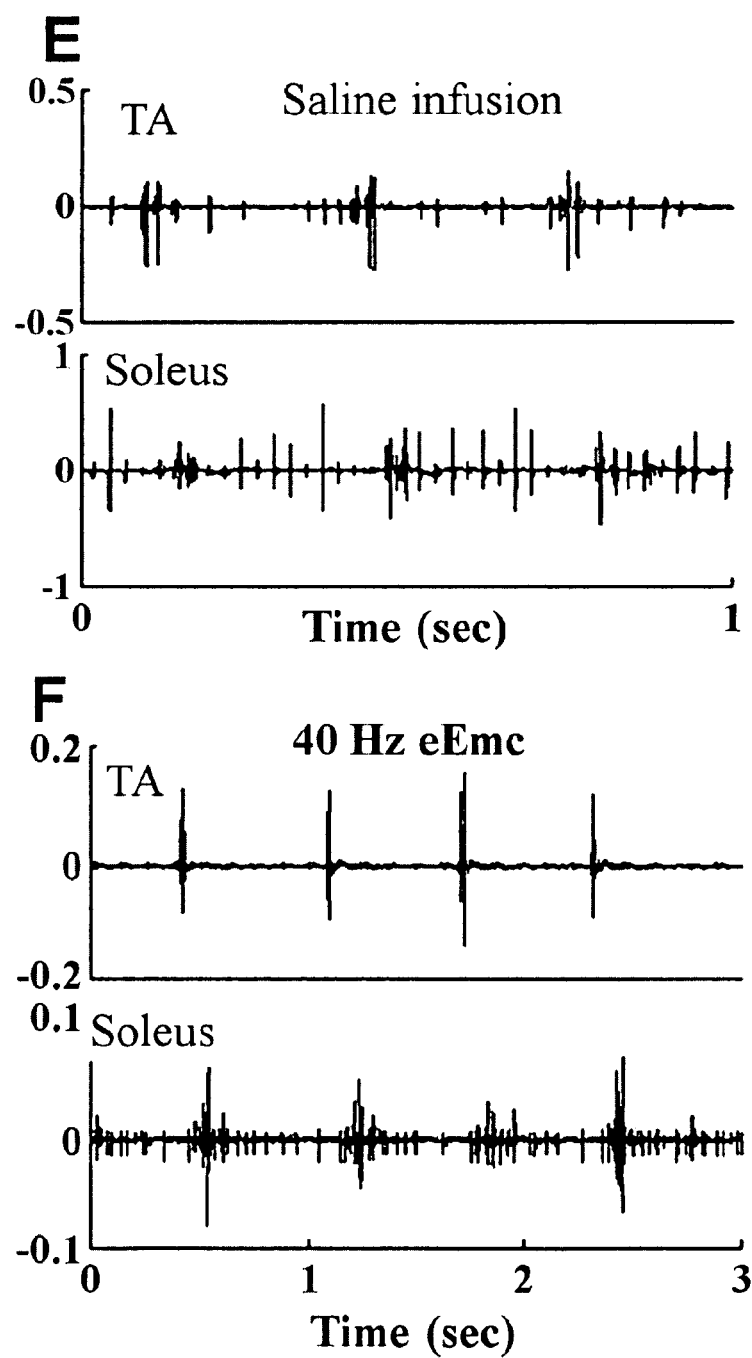
Fig. 1, cont'd.

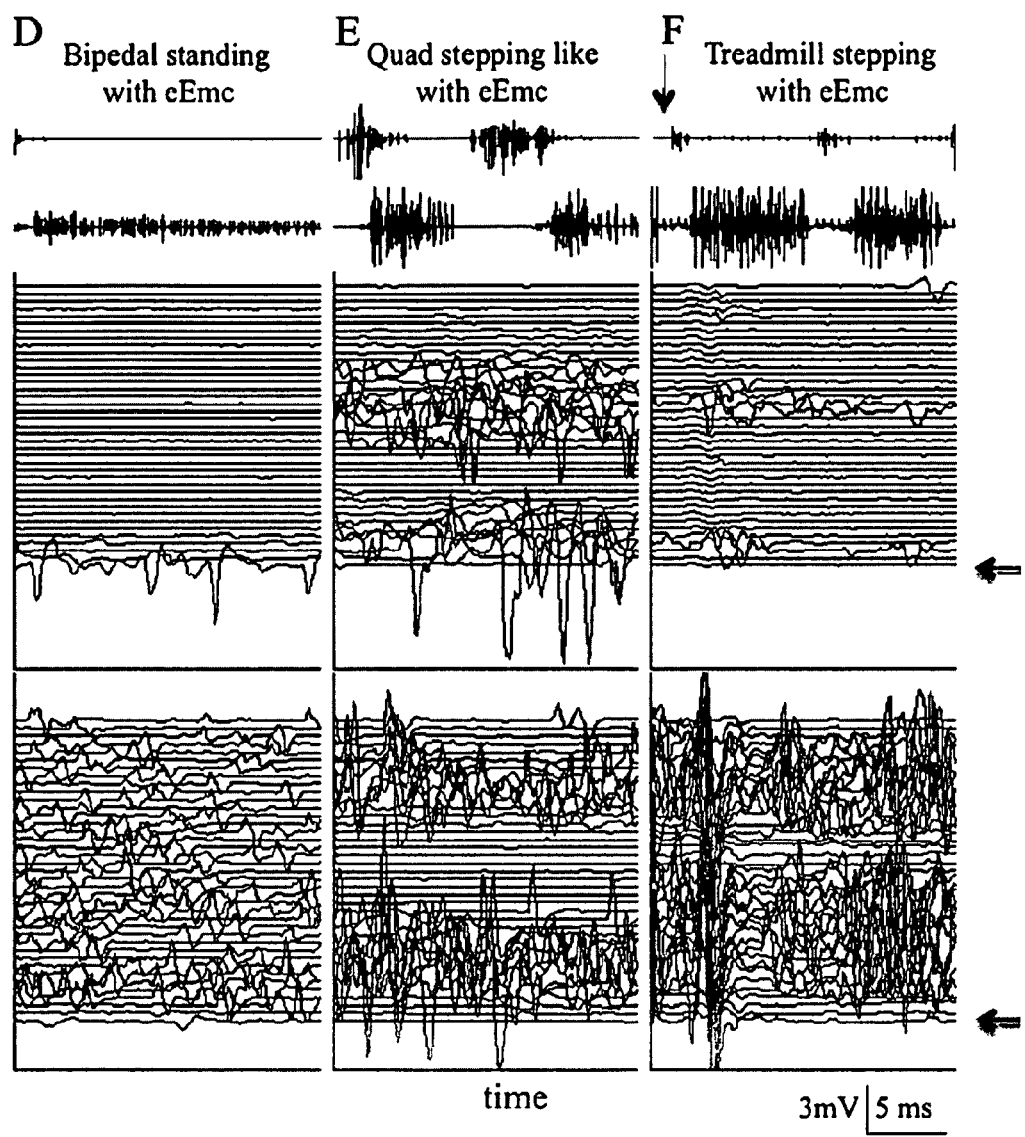
Fig. 7, cont'd.

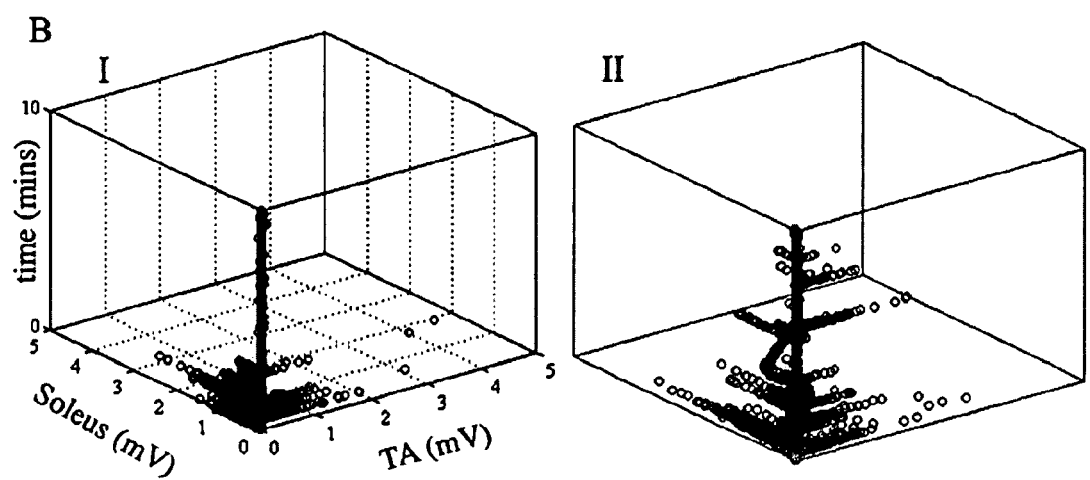
Fig. 12, cont'd.

REGULATION OF AUTONOMIC CONTROL OF BLADDER VOIDING AFTER A COMPLETE SPINAL CORD INJURY

CROSS-REFERENCE TO RELATED APPLICATIONS

This application is a U.S. 371 National Phase of PCT/US2015/046378, filed on Aug. 21, 2015, which claims benefit of and priority to U.S. Ser. No. 62/040,334, filed on Aug. 21, 2014, all of which are incorporated herein by reference in their entirety for all purposes.

STATEMENT OF GOVERNMENTAL SUPPORT

This invention was made with government support under Grant No. EB007615, awarded by the National Institutes of Health. The government has certain rights in the invention.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

The main functions of the lower urinary tract that are compromised after a spinal cord injury (SCI) are the ability to store and to expel urine in a coordinated, controlled manner (de Groat et al. (1998) *Behav. Brain Res.* 92: 127-140; Shefchyk (2002) *Progr. Brain Res.* 137: 71-82). In the normal adult rat, storage of urine is dependent on the inhibition of parasympathetic action on the smooth bladder muscle (detrusor) and on the sympathetic tonic activation of the internal urethral sphincter for outflow resistance. During micturition, efficient voiding is dependent on synchronous activation of the detrusor muscle for contraction, relaxation of the internal urethral sphincter, and bursting activity of the striated external urethral sphincter (EUS) for enhanced urine flow (Maggi et al. (1986) *J. Pharmacol. Meth.*, 15: 157-167; Kruse et al. (1993) *Am J. Physiol.-Regul. Integrative and Comp. Physiol.*, 264: 1157-1163). In humans conscious control of the initiation of these largely autonomic functions involves a complex interaction between the cerebral cortex, pontine micturition center, sympathetic and parasympathetic nervous systems, and somatic motoneurons in the lumbar spinal cord. This interaction simultaneously activates stereotypical postural adjustments that are specie as well as gender unique.

Over the past several decades, multiple techniques have been used to induce micturition after SCI, including stimulation of the bladder wall, the pelvic nerve, and/or the sacral nerve. Directly stimulating the bladder wall induces local contractions, but high currents or a large number of electrodes are needed to induce a more widespread contraction to achieve sufficient bladder emptying. Pelvic nerve stimulation has been shown to contract the bladder wall, but as the pelvic nerve does not innervate the EUS minimal effect was seen on the EUS resulting in a low voiding efficiency (Holmquist and Tord (1968) *Scand. J. Urol. Nephrol.* 2: 129-135). Voiding was only achieved, however, by cutting the pudental nerve. This largely irreversible procedure eliminates sensation from the external genitalia of both sexes and the skin around the anus and perineum, as well as the motor supply to various pelvic muscles, including the external urethral sphincter and the external anal sphincter. Sacral nerve stimulation seemed to offer the best results, but requires complicated surgical procedures and a serious risk of permanent damage via the intradural approach (Rijkhoff et al. (1997) *J. Urol.*, 157: 1504-1508).

SUMMARY

In various embodiments methods and devices are provided to provide improved regulation/control of bladder voiding in a subject with impaired bladder control. In certain embodiments the subject is a subject with a spinal cord or brain injury, or a neurological injury or illness. It was discovered that electrical stimulation of the lumbosacral spinal cord can improve initiation of micturition and/or improve the consistency and/or amount of bladder emptying.

Various embodiments contemplated herein may include, but need not be limited to, one or more of the following:

Embodiment 1

A method of improving bladder function in a subject with impaired bladder control, said method including applying a pattern of electrical stimulation to the lumbosacral spinal cord at a frequency and intensity sufficient to initiate micturition and/or to improve the amount of bladder emptying.

Embodiment 2

The method of embodiment 1, wherein said subject has a spinal cord or brain injury or a neurological injury or illness.

Embodiment 3

The method according to any one of embodiments 1-2, wherein said electrical stimulation is at a frequency and intensity sufficient to initiate micturition.

Embodiment 4

The method according to any one of embodiments 1-3, wherein said electrical stimulation is at a frequency and intensity sufficient to improve the amount of bladder emptying (e.g., to provide at least 30% emptying or at least 40% emptying, or at least 50% emptying, or at least 60% emptying, or at least 70% emptying, or at least 80% emptying, or at least 90% emptying, or at least 95% emptying).

Embodiment 5

The method according to any one of embodiments 1-4, wherein bladder emptying is initiated within 10 seconds, or within 5 seconds, or within 3 seconds, or within 2 seconds, or within 1 second of initiation of electrical stimulation.

Embodiment 6

The method according to any one of embodiments 1-5, wherein said electrical stimulation is over a region of the spinal cord including or consisting of the region from L1 to S5 or from L1 to S3, or from L1 to S1, or from L2 to S1.

Embodiment 7

The method according to any one of embodiments 1-5, wherein said electrical stimulation is over a region of the spinal cord including or consisting of the region from L2 to S1.

Embodiment 8

The method according to any one of embodiments 1-7, wherein said electrical stimulation ranges from about 1 Hz up to about 100 Hz, or from about 1 Hz up to about 50 Hz, or from about 1 Hz up to about 40 Hz, or is about 1 Hz.

Embodiment 9

The method according to any one of embodiments 1-7, wherein said electrical stimulation ranges from about 1 Hz up to about 40 Hz, or is about 1 Hz.

Embodiment 10

The method according to any one of embodiments 1-9, wherein said electrical stimulation includes tonic stimulation.

Embodiment 11

The method according to any one of embodiments 1-10, wherein said electrical stimulation includes bipolar stimulation.

Embodiment 12

The method according to any one of embodiments 1-11, wherein said electrical stimulation includes epidural electrical stimulation.

Embodiment 13

The method of embodiment 12, wherein said epidural electrical stimulation is at an amplitude ranging from about 0.01 mA or about 0.05 mA to about 50 mA or to about 30 mA, or from about 0.1 mA to about 20 mA, or from about 0.1 mA to about 15 mA or to about 10 mA.

Embodiment 14

The method according to any one of embodiments 12-13, wherein said epidural stimulation comprise pulses having a pulse width ranging from about 1 µs to about 1 ms, or from about 1 µs or about 10 µS, or from about 100 µs to about 1 ms, or from about 150 µs to about 600 µs, or from about 200 µs to about 500 µs, or from about 200 µs to about 450 µs.

Embodiment 15

The method according to any one of embodiments 12-14, wherein said epidural stimulation is applied via a permanently implanted electrode array.

Embodiment 16

The method of embodiment 15, wherein said electrode array is a polymer based microelectrode implant.

Embodiment 17

The method of embodiment 15, wherein said electrode array is a parylene or polyimide based microelectrode implant.

Embodiment 18

The method according to any one of embodiments 1-11, wherein said electrical stimulation includes transcutaneous electrical stimulation.

Embodiment 19

The method of embodiment 18, wherein said transcutaneous stimulation is at an amplitude ranging from 10 mA up to about 300 mA, or up to about 150 mA, or up to about 100 mA, or from about 20 mA to about 300 mA, or up to about 150 mA or up to about 100 mA, or from about 20 mA or from about 30 mA, or from about 40 mA up to about 50 mA, or up to about 60 mA, or up to about 70 mA or up to about 80 mA, or up to about 100 mA, or up to about 150 mA, or up to about 200 mA, or up to about 250 mA, or up to about 300 mA.

Embodiment 20

The method according to any one of embodiments 18-19, wherein said transcutaneous stimulation pulse width ranges from about 10 µs, or from about 50 µs, or from about 100 µs, or from about 250 µs, up to about 1000 µs, or up to about 500 µs, or up to about 250 µs, or up to about 200 µs.

Embodiment 21

The method according to any one of embodiments 18-20, wherein said transcutaneous stimulation is superimposed on a high frequency carrier signal.

Embodiment 22

The method of embodiment 21, wherein said high frequency carrier signal ranges from 3 kHz, or about 5 kHz, or about 8 kHz up to about 80 kHz, or up to about 50 kHz, or up to about 40 kHz, or up to about 30 kHz, or up to about 20 kHz, or up to about 15 kHz.

Embodiment 23

The method of embodiment 21, wherein said high frequency carrier signal is about 10 kHz.

Embodiment 24

The method according to any one of embodiments 21-23, wherein said carrier frequency amplitude ranges from about 30 mA, or about 40 mA, or about 50 mA, or about 60 mA, or about 70 mA, or about 80 mA up to about 500 mA, or up to about 300 mA, or up to about 200 mA, or up to about 150 mA.

Embodiment 25

The method according to any one of embodiments 1-24, wherein said method does not comprise direct stimulation of the pelvic nerve.

Embodiment 26

The method according to any one of embodiments 1-25, wherein said method does not comprise transection of the pudendal nerve.

Embodiment 27

The method according to any one of embodiments 1-26, wherein said method does not comprise direct stimulation of the sacral nerve.

Embodiment 28

The method according to any one of embodiments 1-27, wherein said method does not comprise direct stimulation of the anterior sacral nerve.

Embodiment 29

The method according to any one of embodiments 1-28, wherein said method includes treating said subject applying a pattern of electrical stimulation in repeated electrical stimulation training sessions.

Embodiment 30

The method of embodiment 29, wherein said repeated electrical stimulation training sessions are repeated over a period of at least one day, or over a period of at least 2 days, or over a period of at least 3 days, or over a period of at least 1 week, or over a period of at least 2 weeks, or over a period of at least 3 weeks, or over a period of at least 4 weeks, or over a period of at least 5 weeks, or over a period of at least 6 weeks.

Embodiment 31

The method according to any one of embodiments 1-30, wherein the subject is a human.

Embodiment 32

The method according to any one of embodiments 1-31, wherein the electrical stimulation is under control of the subject.

Embodiment 33

The method according to any one of embodiments 1-32, wherein said method further includes physical training of said subject.

Embodiment 34

The method of embodiment 33, wherein said physical training includes movement of a region of the torso and/or legs of the subject.

Embodiment 35

The method of embodiment 34, wherein said movement includes a change in postural position.

Embodiment 36

The method of embodiment 34, wherein said movement includes a locomotor activity associated with standing and/or stepping and/or sitting.

Embodiment 37

The method according to any one of embodiments 33-36, wherein said training includes training against a resistance.

Embodiment 38

The method according to any one of embodiments 33-37, wherein said training is robotically facilitated.

Embodiment 39

The method according to any one of embodiments 33-38, wherein said training utilizes a treadmill and/or an exoskeleton, and/or a prosthesis.

Embodiment 40

The method according to any one of embodiments 1-39, wherein said method further includes administration of a drug selected from the group consisting of a serotonergic drug, a dopaminergic drug, a noradrenergic drug, a GABAergic drug, and a glycinergic drug.

Embodiment 41

The method of embodiment 40, wherein said drug is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclo-hexanecarboxamide (WAY 100.635), quipazine, strychnine, ketanserin, 4-amino-(6-chloro-2-pyridyl)-1 piperidine hydrochloride (SR 57227A), Ondanesetron, buspirone, methoxamine, prazosin, clonidine, yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), quinpirole, and eticlopride.

Embodiment 42

The method of embodiment 41, wherein said drug includes buspirone.

Embodiment 43

The method of embodiment 41, wherein said drug includes quipazine and/or strychnine.

Embodiment 44

The method according to any one of embodiments 1-43, wherein said subject has a spinal cord injury.

Embodiment 45

The method of embodiment 44, wherein said spinal cord injury is a thoracic or cervical spinal cord injury.

Embodiment 46

The method according to any one of embodiments 44-45, wherein said spinal cord injury is clinically classified as motor complete.

Embodiment 47

The method according to any one of embodiments 44-45, wherein said spinal cord injury is clinically classified as motor incomplete.

Embodiment 48

The method according to any one of embodiments 1-43, wherein said subject has an ischemic brain injury.

Embodiment 49

The method of embodiment 48, wherein said ischemic brain injury is brain injury from stroke or acute trauma.

Embodiment 50

The method according to any one of embodiments 1-43, wherein said subject has a neurodegenerative pathology.

Embodiment 51

The method of embodiment 50, wherein said neurodegenerative pathology is associated with a condition selected from the group consisting of Parkinson's disease, Huntington's disease, Alzheimer's disease, amyotrophic lateral sclerosis (ALS), primary lateral sclerosis (PLS), and cerebral palsy.

Embodiment 52

A method training a subject having a spinal cord and/or brain injury, to improve initiation of micturition and/or to improve the amount of bladder emptying, said method including: administering to said subject repeated electrical stimulation training sessions according to any one of embodiments 1-28.

Embodiment 53

The method of embodiment 52, where said training sessions are administered until the response of said subject to electrical stimulation provides improved initiation of micturition (e.g., improved consistency) and/or increased voiding of the bladder.

Embodiment 54

The method according to any one of embodiments 52-53, wherein said repeated electrical stimulation training sessions are repeated over a period of at least one day, or over a period of at least 2 days, or over a period of at least 3 days, or over a period of at least 1 week, or over a period of at least 2 weeks, or over a period of at least 3 weeks, or over a period of at least 4 weeks, or over a period of at least 5 weeks, or over a period of at least 6 weeks.

Embodiment 55

The method according to any one of embodiments 52-54, wherein the subject is a human.

Embodiment 56

The method according to any one of embodiments 52-55, wherein the electrical stimulation is under control of the subject.

Embodiment 57

The method according to any one of embodiments 52-56, wherein said method further includes physical training of said subject.

Embodiment 58

The method of embodiment 57, wherein said physical training includes movement of a region of the torso and/or legs of the subject.

Embodiment 59

The method of embodiment 58, wherein said movement includes a change in postural position.

Embodiment 60

The method of embodiment 58, wherein said movement includes a locomotor activity associated with standing and/or stepping and/or sitting.

Embodiment 61

The method according to any one of embodiments 57-60, wherein said training includes training against a resistance.

Embodiment 62

The method according to any one of embodiments 57-61, wherein said training is robotically facilitated.

Embodiment 63

The method according to any one of embodiments 57-62, wherein said training utilizes a treadmill and/or an exoskeleton, and/or a prosthesis.

Embodiment 64

The method according to any one of embodiments 52-63, wherein said method further includes administration of a drug selected from the group consisting of a serotonergic drug, a dopaminergic drug, a noradrenergic drug, a GABAergic drug, and a glycinergic drug.

Embodiment 65

The method of embodiment 64, wherein said drug is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclohexanecarboxamide (WAY 100.635), quipazine, strychnine, ketanserin, 4-amino-(6-chloro-2-pyridyl)-1 piperidine hydrochloride (SR 57227A), Ondanesetron, buspirone, methoxamine, prazosin, clonidine, yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), quinpirole, and eticlopride.

Embodiment 66

The method of embodiment 65, wherein said drug includes buspirone.

Embodiment 67

The method of embodiment 65, wherein said drug includes quipazine and/or strychnine.

Embodiment 68

The method according to any one of embodiments 52-67, wherein said subject has a spinal cord injury.

Embodiment 69

The method of embodiment 68, wherein said spinal cord injury is a thoracic or cervical spinal cord injury.

Embodiment 70

The method according to any one of embodiments 68-69, wherein said spinal cord injury is clinically classified as motor complete.

Embodiment 71

The method according to any one of embodiments 68-69, wherein said spinal cord injury is clinically classified as motor incomplete.

Embodiment 72

The method according to any one of embodiments 52-67, wherein said subject has an ischemic brain injury.

Embodiment 73

The method of embodiment 72, wherein said ischemic brain injury is brain injury from stroke or acute trauma.

Embodiment 74

The method according to any one of embodiments 52-67, wherein said subject has a neurodegenerative pathology.

Embodiment 75

The method of embodiment 74, wherein said neurodegenerative pathology is associated with a condition selected from the group consisting of Parkinson's disease, Huntington's disease, Alzheimer's disease, amyotrophic lateral sclerosis (ALS), primary lateral sclerosis (PLS), and cerebral palsy.

Embodiment 76

A system for controlling and/or improving bladder function in a mammal, said system including a transcutaneous electrode and/or an epidural electrode electrically coupled to an electrical stimulator configured to deliver transcutaneous electrical stimulation of the lumbosacral spinal cord through a transcutaneous electrode and/or epidural electrical stimulation of the lumbosacral spinal cord through an epidural electrode according to the method of any one of embodiments 1-27.

Embodiment 77

The system of embodiment 76, wherein said system includes an electrical stimulator coupled to an epidural electrode configured to deliver epidural stimulation according to the method of any one of embodiments 1-14.

Embodiment 78

The system of embodiment 77, wherein said epidural electrode includes a permanently implanted electrode array.

Embodiment 79

The system of embodiment 78, wherein said electrode array is a polymer based microelectrode implant.

Embodiment 80

The system of embodiment 78, wherein said electrode array is a parylene or polyimide based microelectrode implant.

Embodiment 81

The system of embodiment 76, wherein said system includes an electrical stimulator coupled to a transcutaneous electrode configured to deliver transcutaneous stimulation according to the method of any one of embodiments 1-11 and 18-24.

Embodiment 82

The system according to any one of embodiments 76-81, wherein said system further comprise a sensor to detect bladder fullness.

Embodiment 83

The system of embodiment 82, wherein said sensor is configured to indicate state of bladder fullness to said subject.

Embodiment 84

The system according to any one of embodiments 82-83, wherein said sensor is coupled to a controller to operate said electrical stimulator to void the bladder at a specified fullness and/or at a specified time and/or in response to a user input.

Embodiment 85

The system according of embodiment 84, wherein said controller is integrated into said stimulator.

Embodiment 86

The system according of embodiment 84, wherein said controller is independent of said stimulator.

Embodiment 87

The system according to any one of embodiments 82-87, wherein said sensor includes a nerve-electrode interface that combines features sieve and cuff designs by confining axons microchannels.

Embodiment 88

The system according to any one of embodiments 76-87, wherein said system that includes a training device configured to assist with physically training of the subject.

Embodiment 89

The system of embodiment 88, wherein said training device includes one or more devices selected from the group consisting of a treadmill, a walker, an exoskeleton, a weight machine, an exoskeleton, and an robotic training device.

Embodiment 90

The system according to any one of embodiments 76-89, wherein said system is configured to record, receive and/or transmit data wirelessly.

Embodiment 91

A method for restoring bladder function in a patient after a spinal cord injury causing paralysis, the method including applying a pattern of electrical stimulation to the spinal cord.

Embodiment 92

The method of embodiment 91, wherein bladder emptying is initiated within seconds of initiation of electrical stimulation.

Embodiment 93

The method of embodiment 91, further including treating the patient with repeated stimulation-training sessions.

Embodiment 94

A method for restoring bladder function in a patient after a spinal cord injury causing paralysis, the method including enabling locomotor-related spinal neuronal circuits by epidural stimulation.

Embodiment 95

The method of embodiment 94, wherein bladder emptying is initiated within seconds of initiation of epidural stimulation.

Embodiment 96

The method of embodiment 94, further including treating the patient with repeated stimulation-training sessions.

Embodiment 97

A method for restoring bladder function in a patient after a spinal cord injury causing paralysis, the method including: placing electrodes epidurally on the dorsum of the spinal cord; energizing the electrodes with a frequency-dependent stimulation pattern that is therapeutically effective.

Embodiment 98

The method of embodiment 97, further including treating the patient with repeated stimulation-training sessions.

Definitions

The terms "patient", "subject", or "mammalian subject" are used interchangeably herein and include any mammal in need of the treatment methods described herein (e.g., methods of bladder control in subjects having a brain and/or spinal cord injury). Such mammals include, particularly humans (e.g., human infants, human teens, human adults, etc.). Other mammals in need of such treatment can include non-human mammals such as dogs, cats, or other domesticated animals, horses, livestock, laboratory animals (e.g., lagomorphs, non-human primates, etc.), and the like. The subject may be male or female.

As used herein "electrical stimulation" or "stimulation" means application of an electrical signal that may be either excitatory or inhibitory to a muscle, nerve, nerve tract, nerve branch, nerve root or neuron and/or to groups of neurons and/or interneurons. It will be understood that an electrical signal may be applied to one or more electrodes with one or more return electrodes.

As used herein "epidural" means situated upon the dura or in very close proximity to the dura. The term "epidural stimulation" refers to electrical epidural stimulation. In certain embodiments epidural stimulation is referred to as "electrical enabling motor control" (eEmc).

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS". The term "pcEmc" refers to painless cutaneous electrical stimulation.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical and/or magnetic stimulation or vice versa). Simultaneous physiological effect need not necessarily require presence of drug and the electrical and/or magnetic stimulation at the same time or the presence of both stimulation modalities at the same time. In some embodiments, all the modalities are administered essentially simultaneously.

The phrase "spinal cord stimulation" as used herein includes stimulation of any spinal nervous tissue, including spinal neurons, accessory neuronal cells, nerves, nerve roots, nerve fibers, or tissues, that are associated with the spinal cord. It is contemplated that spinal cord stimulation may comprise stimulation of one or more areas associated with a lumbosacral vertebral segment.

As used herein, "spinal nervous tissue" refers to nerves, neurons, neuroglial cells, glial cells, neuronal accessory cells, nerve roots, nerve fibers, nerve rootlets, parts of nerves, nerve bundles, mixed nerves, sensory fibers, motor fibers, dorsal root, ventral root, dorsal root ganglion, spinal ganglion, ventral motor root, general somatic afferent fibers, general visceral afferent fibers, general somatic efferent fibers, general visceral efferent fibers, grey matter, white matter, the dorsal column, the lateral column(s), and/or the ventral column associated with the spinal cord. Spinal nervous tissue includes "spinal nerve roots," that comprise any one or more of the 31 pairs of nerves that emerge from the spinal cord.

DETAILED DESCRIPTION

Figure 1:
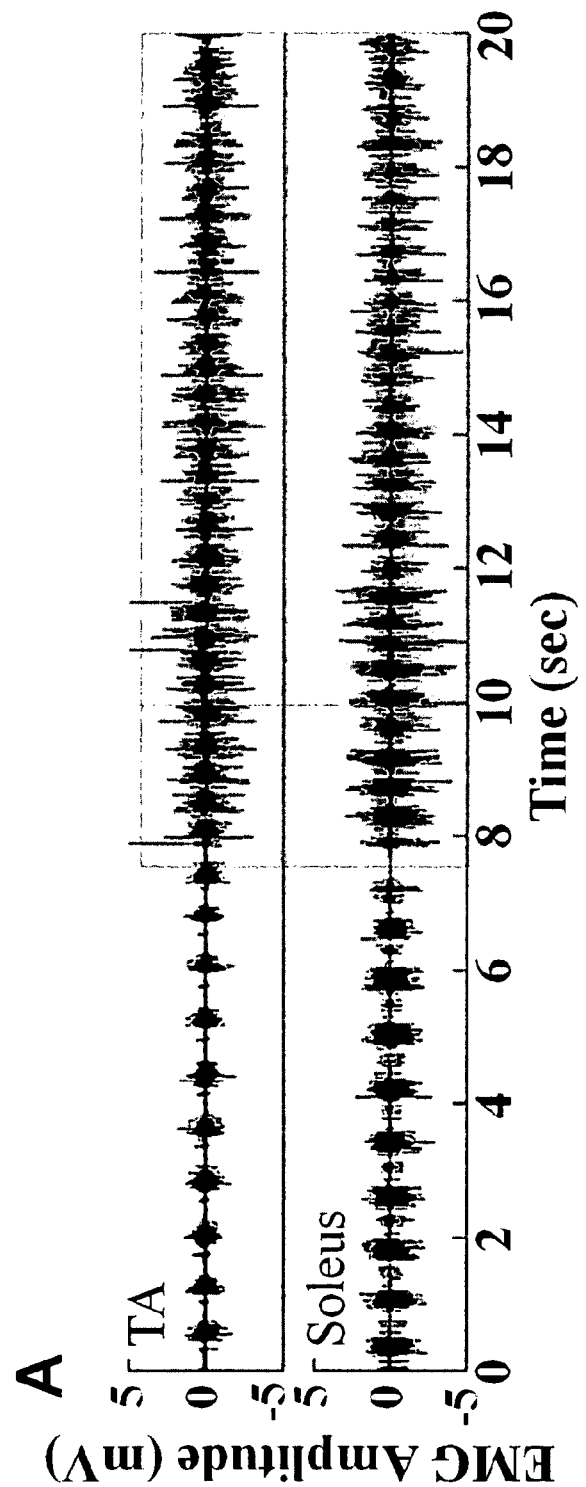
FIG. 1. Panel A: Representative EMG recordings from the soleus and tibialis anterior (TA) muscles from a spinal rat suspended in a harness and stepping bipedally on a treadmill at 13.5 cm/s under the influence of eEmc (40 Hz between L2 and S1). The rat begins to micturate at the beginning of the green shaded area. Note the shorter step cycle periods and higher EMG amplitudes a few steps prior to (red shaded area) and during (green shaded area) micturition. Panel B: EMG amplitude distribution plots showing an increase in the amount of co-activation of the soleus and TA muscles during the steps immediately before and during micturition. Panel C: Step cycle duration and soleus and TA integrated EMG (iEMG) for each step in panel A. Panel D: Mean (±SEM) step cycle duration and soleus and TA EMG burst durations for the regions in panel A. Representative EMG recordings from the soleus and TA muscles when the rat hindlimbs were suspended above the treadmill belt (unloaded) during saline infusion (1 cc) into the bladder via a urethral catheter (panel E) or 40 Hz eEmc (panel F).

In various embodiments methods, devices and systems are provided to facilitate bladder control in a subject (e.g., a human or a non-human mammal) that has a spinal cord or brain injury. In various embodiments training methods are provided that improve the response of a subject to the methods, devices and systems that facilitate bladder control.

It is demonstrated that long-term synergistic effects of epidural stimulation have beneficial effects on bladder function. Additionally, specific spinal cord stimulation parameters are identified that initiate bladder emptying within seconds of the initiation of, e.g., epidural electrical stimulation.

Given the locations of the neural networks within the spinal cord that control autonomic function, the level and extent of a spinal cord lesion are important factors in the extent of loss of bladder function (Potter (2006) *Progr. Brain Res.* 152: 51-57). A complete mid-thoracic spinal cord transection in rats results in the loss of bladder function initially with some autonomically initiated spontaneous control returning in the following weeks, allowing for occasional but incomplete emptying. In humans with a thoracic or cervical SCI, descending projections from supraspinal centers often are severed and their axons degenerated. In many such individuals, the reflex pathways mediating continence remain intact, but micturition cannot be initiated in a normal manner (Barrington (1941) *Brain,* 64: 239-243). The most common form of this condition is detrusor-sphincter dyssynergia (de Groat et al. (1990) *J. Autonom. Nervous Syst.* 30: 71-77; de Groat and Yoshimura (2010) *Neuro. & Urodynam.* 29: 63-76) in which both the detrusor and EUS tend to be activated together rather than reciprocally.

As demonstrated herein, it appears that epidural stimulation raises the net excitability level of spinal neural networks (interneurons and motoneurons) and, particularly when combined with motor training and/or pharmacological interventions, enhances the activation of the sensorimotor pathways that also control bladder function. Data presented herein demonstrate that in addition to the chronic effects, e.g., improved spontaneous bladder emptying associated with epidural stimulation and, for example step training, a unique spinal epidural stimulation paradigm is described that can overcome detrusor-sphincter dyssynergia and induce bladder emptying on demand in subjects with a complete mid-thoracic spinal cord transection.

It is noted that within three days of the initiation of epidural stimulation and step training the rats started voiding spontaneously during cage activity and step training. After 3 weeks of locomotor training facilitated with eEmc (40 Hz between L2 and S1) and quipazine and strychnine administration, the spinal rats consistently voided when stimulated at 1 Hz between L2 and S1. Without being bound to a particular theory, it is believed that locomotor training (Courtine et al. (2009) *Nature Neurosci.* 12: 1333-1342; Ichiyama et al. (2008) *J Neurosci.* 28: 7370-7375) with eEmc chronically engaged the neural networks by lowering the threshold of excitability and apparently when stimulated at 1 Hz the networks were tuned to initiate micturition.

An underlying mechanism of the improved spontaneous control of bladder emptying is suggested by the heightened responses to the afferent-information sensing bladder volume. This enhanced spontaneous voiding of the bladder was more efficient in the trained compared to untrained animals most likely reflecting the lowered activation threshold due to the chronic engagement of the neural networks in the trained rats.

In certain embodiments the complex functioning of bladder voiding was achieved via an eEmc tonic drive at 1 Hz between L2 and S1, although as demonstrated herein other stimulation patterns also facilitate micturation. The conceptual basis of selecting a given eEmc parameter was to activate the neural networks that initiate the automaticity of the coordinated contractions and relaxations of the bladder and EUS that result in bladder voiding. During stimulation at 1 Hz, the bladder contracts tonically. This response occurs in the EUS within a 20 to 100 ms time window. Without being bound to a particular theory, it is believed that these evoked potentials with a long latency may represent the activation of complex interneuronal networks that enable bursting activity of the EUS similar to that observed during voiding in intact rats.

In the methods described herein, by preserving the sensorimotor networks that underlie the automaticity of micturition, as occurs with the recovery of stepping and standing after a complete spinal cord transection, bladder function can be largely re-established by enabling the inherent automaticity present within the spinal cord. As demonstrated herein, the spinal cord circuitry contains the necessary circuitry to control bladder voiding when provided the appropriate afferent information from the bladder and the sphincter. Based on frequency-specific stimulation parameters, the spinal cord can be tuned to enable the appropriate physiological response.

The clinical implications of this technique are immense and parallel the impact that spinal cord stimulation has had on locomotion studies and the recovery of volitional movement after complete paralysis (Harkema et al. (2011) *Lancet,* 377: 1938-1947; Angeli et al. (2014) *Brain,* 137: 1394-1409). The application of spinal cord stimulation to overcome difficulty in micturition is not likely limited to SCI but could be adapted to other neurological and/or physiological disorders. This protocol could be invaluable in avoiding unnecessary transurethral catheterization, potentially lowering the incidence of urinary tract infections and reversing the uptake of urine into the kidney.

In summary, the main findings include, but are not limited to 1) the demonstration of functional links between the neural control (biomechanical and electrophysiological) of locomotion and micturition in awake unanesthetized rats, 2) the immediate effect of in vivo spinal cord stimulation on micturition, and 3) the positive chronic effects of step training under the influence of eEmc and pharmacological interventions on bladder function.

Accordingly, in various embodiments, methods of providing/improving bladder function in a subject after a spinal cord and/or brain injury are provided where the methods comprise applying a pattern of electrical stimulation to the lumbosacral spinal cord at a frequency and intensity sufficient to facilitate micturation. Such facilitation may include inter alia, improvement in initiation of micturition and/or improvement in the volume of the bladder that is voided. Thus, in certain embodiments, the method provided herein provide at least 30% emptying or at least 40% emptying, or at least 50% emptying, or at least 60% emptying, or at least 70% emptying, or at least 80% emptying, or at least 90% emptying, or at least 95% emptying, or at least 98% emptying of the bladder, e.g., upon application of electrical stimulation as described herein. In certain embodiments the stimulation comprises epidural electrical stimulation, while in other embodiments the stimulation comprises transcutaneous electrical stimulation.

In certain embodiments the methods described herein can further involve physical training of the subject. In certain embodiments such training can include, inter alia, movement of a region of the torso and/or legs of the subject (and/or stabilization of a region of the torso and/or legs against a resistance).

In certain embodiments the methods can also further involve administration of a neuromodulatory drug (e.g., a serotonergic drug, a dopaminergic drug, a noradrenergic drug, a GABAergic drug, and/or a glycinergic drug). Illustrative drugs include, but are not limited to buspirone, quipazine and/or strychnine.

It was also a surprising discovery that a training regime comprising repeated bouts of electrical stimulation (e.g., as described herein) can produce improvements in micturition. Thus for example, consistency of micturition initiation, e.g., in response to electrical stimulation, and/or improvements in voiding volume can be improved by such repeated electrical stimulation training bouts optionally in combination with physical training and/or administration of drugs as described herein.

In certain embodiments systems are provided for, inter alia, controlling bladder function. In illustrative, but non-limiting embodiments, the systems comprise a transcutaneous electrode and/or an epidural electrode electrically coupled to an electrical stimulator configured to deliver transcutaneous electrical stimulation of the lumbosacral spinal cord through a transcutaneous electrode and/or epidural electrical stimulation of the lumbosacral spinal cord through an epidural electrode according to the method described herein. In certain embodiments the system comprise a sensor to detect bladder fullness.

In various embodiments the methods described herein are advantageous in that they do not require transection of the pudendal nerve and thereby avoid the adverse consequences of such transection. In various embodiments the methods described herein, surprisingly, do not require direct stimulation of the pelvic nerve and/or the sacral nerve.

Epidural Stimulation of a Region of the Lumbosacral Spine

In various embodiments, the methods described herein involve epidural electrical stimulation of the lumbosacral spine or a region of the lumbosacral spine of the subject. Illustrative regions include, but are not limited to one or more regions straddling or spanning a region selected from the group consisting of L1-L1, L1-L2, L1-L3, L1-L4, L1-L5, L1-S1, L1-S2, L1-S3, L1-S4, L1-55, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-55, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

In certain embodiments the epidural stimulation is at a frequency ranging from about 0.5 Hz or from about 1 Hz up to about 100 Hz, or from about 1 Hz up to about 50 Hz, or from about 1 Hz up to about 40 Hz, or from about 1 Hz, or from about 5 Hz, or from about 10 Hz up to about 100 Hz, or up to about 80 Hz, or up to about 50 Hz, or up to about 40 Hz.

In certain embodiments the epidural stimulation is at an amplitude ranging from 0.05 mA up to about 30 mA, or from about 0.1 mA up to about 20 mA, or from about 0.1 mA up to about 15 mA or up to about 10 mA.

In certain embodiments the pulse width ranges from about 1 μs, or from about 10 μs, or from about 100 μs, or from about 150 μs up to about 600 μs, or up to about 500 μs, or up to about 250 μs, or up to about 150 μs, or up to about 100 μs, or from about 1 μs to about 1 ms, or from about 1 μs or from about 10 μS, or from about 100 μs to about 1 ms, or from about 150 μs to about 600 μs, or from about 200 μs to about 500 μs, or from about 200 μs to about 450 μs. In certain embodiments the pulse width ranges from about 100 μs up to about 1000 μs.

In certain embodiments the epidural stimulation is at a frequency and amplitude sufficient to initiate bladder emptying and/or to improve the degree of bladder emptying. In certain embodiments the epidural stimulation is at a frequency and amplitude sufficient to provide at least 30% emptying or at least 40% emptying, or at least 50% emptying, or at least 60% emptying, or at least 70% emptying, or at least 80% emptying, or at least 90% emptying, or at least 95% emptying, or at least about 98% emptying of the bladder.

In certain embodiments the epidural stimulation is applied paraspinally over a lumbosacral identified above (e.g., over vertebrae spanning L2 to S1, etc.).

In certain embodiments the epidural stimulation is applied via a permanently implanted electrode array (e.g., a typical density electrode array, a high density electrode array, etc.).

In certain embodiments the epidural electrical stimulation is administered via a high density epidural stimulating array (e.g., as described in PCT Publication No: WO/2012/094346 (PCT/US2012/020112). In certain embodiments, the high density electrode arrays are prepared using microfabrication technology to place numerous electrodes in an array configuration on a flexible substrate. One suitable epidural array fabrication method was first developed for retinal stimulating arrays (see, e.g., Maynard (2001) *Annu. Rev. Biomed. Eng.*, 3: 145-168; Weiland and Humayun (2005) *IEEE Eng. Med. Biol. Mag.*, 24(5): 14-21, and U.S. Patent Publications 2006/0003090 and 2007/0142878). In various embodiments the stimulating arrays comprise one or more biocompatible metals (e.g., gold, platinum, chromium, titanium, iridium, tungsten, and/or oxides and/or alloys thereof) disposed on a flexible material (e.g., parylene A, parylene C, parylene AM, parylene F, parylene N, parylene D, or other flexible substrate materials). Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, Medical Device and Diagnostic Industry, 22(8): 42-49 (2000)), and has flexibility characteristics (Young's modulus ~4 GPa (Rodger and Tai (2005) *IEEE Eng. Med. Biology*, 24(5): 52-57)), lying in between those of PDMS (often considered too flexible) and most polyimides (often considered too stiff). Finally, the tear resistance and elongation at break of parylene are both large, minimizing damage to electrode arrays under surgical manipulation (Rodger et al. (2006) *Sensors and Actuators B-Chemical*, 1 17(1): 107-114). Microelectrode arrays and the preparation such microelectrode arrays suitable for use in the epidural stimulation methods described herein is described in PCT Publication No: WO/2012/100260 (PCT/US2012/022257).

The electrode array may be implanted using any of a number of methods (e.g., a laminectomy procedure) well known to those of skill in the art.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

Any present or future developed stimulation system capable of providing an electrical signal to one or more regions of the lumbosacral spinal cord may be used in accordance with the teachings provided herein. In various embodiments, the system may comprise an external pulse generator. In other embodiments the system may comprise an implantable pulse generator to produce a number of stimulation pulses that are sent to the a region in proximity to the lumbosacral spinal cord (e.g., L2-S1) by insulated leads coupled to the spinal cord by one or more electrodes and/or an electrode array. In certain embodiments the one or more electrodes or one or more electrodes comprising the electrode array may be attached to separate conductors included within a single lead. Any known or future developed lead useful for applying an electrical stimulation signal in proximity to a subject's spinal cord may be used. For example, the leads may be conventional percutaneous leads, such as PISCES® model 3487A sold by Medtronic, Inc. In certain circumstances it may be desirable to employ a paddle-type lead.

Any known or future developed external or implantable pulse generator may be used in accordance with the teachings provided herein. For example one internal pulse generator may be an ITREL® II or Synergy pulse generator available from Medtronic, Inc, Advanced Neuromodulation Systems, Inc.'s GENESIS® pulse generator, or Advanced Bionics Corporation's PRECISION® pulse generator. One of skill in the art will recognize that the above-mentioned pulse generators may be advantageously modified to deliver therapy in accordance with the teachings provided herein.

In certain embodiments the system can employ a programmer coupled via a conductor to a radio frequency antenna. This system permits attending medical personnel to select the various pulse output options after implant using radio frequency communications. While, in certain embodiments, the system employs fully implanted elements, systems employing partially implanted elements may also be used in accordance with the teachings provided herein.

In one illustrative but non-limiting system a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to implantation or receive instructions from a programmer (or another source) through any known or future developed mechanism, such as telemetry. The control module may include or be operably coupled to memory to store instructions for controlling the signal generation module and may contain a processor for controlling which instructions to send to signal generation module and the timing of the instructions to be sent to signal generation module. In various embodiments leads are operably coupled to a signal generation module such that a stimulation pulse generated by a signal generation module may be delivered via electrodes.

While in certain embodiments, two leads are utilized, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in a region of the lumbosacral spine (e.g., L2-S1). A return electrode such as a ground or other reference electrode can be located on the same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

The epidural electrode stimulation systems described above are intended to be illustrative and non-limiting. Using the teachings provided herein alternative epidural stimulation systems and methods will be available to one of skill in the art.

Transcutaneous Stimulation of the Lumbosacral Spinal Cord.

In various embodiments, the methods described herein involve transcutaneous electrical stimulation of the lumbosacral spine or a region of the lumbosacral spine of the subject. Illustrative regions include, but are not limited to one or more regions straddling or spanning a region selected from the group consisting of L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-55, S1-S1, S1-S2, S1-S3, S1-S4, S1-55, S2-S2, S2-S3, S2-S4, S2-S5, S3-S3, S3-S4, S3-S5, S4-S4, and S4-S5.

In certain embodiments, the transcutaneous al stimulation is at a frequency ranging from about 0.5 Hz or from about 1 Hz up to about 100 Hz, or from about 1 Hz up to about 50 Hz, or from about 1 Hz up to about 40 Hz, or from about 1

Hz, or from about 5 Hz, or from about 10 Hz up to about 100 Hz, or up to about 80 Hz, or up to about 50 Hz, or up to about 40 Hz.

In certain embodiments, the transcutaneous stimulation is applied at an intensity (amplitude) ranging from about 10 mA, or from about 20 mA, or from about 30 mA, up to about 300 mA, or up to about 150 mA, or up to about 100 mA, or from about 20 mA up to about 300 mA, or up to about 200 mA, or up to about 150 mA or up to about 100 mA, or from about 20 mA or from about 30 mA, or from about 40 mA up to about 50 mA, or up to about 60 mA, or up to about 70 mA or up to about 80 mA, or up to about 100 mA, or up to about 150 mA, or up to about 200 mA, or up to about 250 mA, or up to about 300 mA. In certain embodiments the intensity ranges from about 50 mA up to about 160 mA.

In certain embodiments, the pulse width ranges from about 10 µs, or from about 50 µs, or from about 100 µs, or from about 250 µs, up to about 500 ms, or up to about 100 ms, or up to about 10 ms, or up to about 1 ms, or up to about 500 µs, or up to about 250 µs, or up to about 200 µs. In certain embodiments the pulse width ranges from about 0.5 up to about 5 ms.

In certain embodiments the stimulation pulse is delivered superimposed on a high frequency carrier signal. In certain embodiments the high frequency ranges from about 3 kHz, or about 5 kHz, or about 8 kHz up to about 100 kHz, or up to about 80 kHz, or up to about 50 kHz, or up to about 40 kHz, or up to about 30 kHz, or up to about 20 kHz, or up to about 15 kHz or up to about 10 kHz. In certain embodiments the carrier frequency amplitude ranges from about 30 mA, or about 40 mA, or about 50 mA, or about 60 mA, or about 70 mA, or about 80 mA up to about 500 mA, or up to about 400 mA, or up to about 300 mA, or up to about 200 mA, or up to about 150 mA.

In one illustrative, but non-limiting embodiment, a bipolar rectangular stimuli (1-msec duration) with a carrier frequency of 10 kHz and at intensities ranging from 30 to 300 mA is used. The stimulation can be at 1 Hz, for example, with an illustrative, but non-limiting exposure duration ranging from 10 to 30 sec. An illustrative, but non-limiting signal intensity is from about 80 mA, or from about 100 mA, or from about 110 mA to about 200 mA, or to about 180 mA, or to about 150 mA.

In certain embodiments the transcutaneous stimulation is at a frequency and amplitude sufficient to initiate bladder emptying and/or to improve the degree of bladder emptying. In certain embodiments the transcutaneous stimulation is at a frequency and amplitude sufficient to provide at least 30% emptying or at least 40% emptying, or at least 50% emptying, or at least 60% emptying, or at least 70% emptying, or at least 80% emptying, or at least 90% emptying, or at least 95% emptying, or at least about 98% emptying of the bladder.

By way of illustration, it is believe non-invasive transcutaneous electrical spinal cord stimulation (tSCS) applied to the lumbosacral spinal cord (e.g., over L2-S1) can induce bladder voiding when applied, e.g., at a frequency ranging from about 1 Hz up to about 40 Hz.

The transcutaneous electrode or electrode array can applied to the surface of a body using any of a number of methods well known to those of skill in the art.

In some embodiments, the subject is provided a generator control unit and is fitted with an electrode(s) and then tested to identify the most effective subject specific stimulation paradigms for facilitation of bladder voiding, e.g., using the herein described stimulation paradigms.

In various embodiments, the system is designed so that the patient can use and control it in the home environment.

In various embodiments, transcutaneous electrodes and/or electrode arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using, e.g., constant current or constant voltage delivery of the stimulation.

It will be recognized that any present or future developed stimulation system capable of providing an electrical signal to one or more regions of the spinal cord may be used in accordance with the teachings provided herein.

In one illustrative but non-limiting system a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), waveform (e.g., square wave, sinusoid, etc.), etc. The control module may be preprogrammed prior to use or receive instructions from a programmer (or another source). Thus, in certain embodiments the pulse generator/controller is configurable by software and the control parameters may be programmed/entered locally, or downloaded as appropriate/necessary from a remote site.

In certain embodiments the pulse generator/controller may include or be operably coupled to memory to store instructions for controlling the stimulation signal(s) and may contain a processor for controlling which instructions to send for signal generation and the timing of the instructions to be sent. In various embodiments the controller may record, receive, and transmit data as well.

While in certain embodiments, two leads are utilized to provide transcutaneous stimulation, it will be understood that any number of one or more leads may be employed. In addition, it will be understood that any number of one or more electrodes per lead may be employed. Stimulation pulses are applied to transcutaneous electrodes and/or electrode arrays (that typically are cathodes) with respect to a return electrode (which typically is an anode) to induce a desired area of excitation of electrically excitable tissue in one or more regions of the spine. A return electrode such as a ground or other reference electrode can be located on the same lead as a stimulation electrode. However, it will be understood that a return electrode may be located at nearly any location, whether in proximity to the stimulation electrode or at a more remote part of the body. It will be further understood that any number of one or more return electrodes may be employed. For example, there can be a respective return electrode for each cathode such that a distinct cathode/anode pair is formed for each cathode.

The methods and devices described herein are effective in a spinal cord injured subject that is clinically classified as motor complete; that is, there is no motor function below the lesion. In various embodiments, the specific combination of electrode(s) activated/stimulated and/or the desired stimulation of any one or more electrodes and/or the stimulation amplitude (strength) can be varied in real time, e.g., by the subject.

In various embodiments, the devices, optional pharmacological agents, and methods are designed so that a subject with partial or no voluntary bladder control can execute effective bladder voiding as desired or necessary.

The transcutaneous electrode stimulation systems described herein are intended to be illustrative and non-limiting. Using the teachings provided herein, alternative transcutaneous stimulation systems and methods will be available to one of skill in the art.

Physical Training.

It was demonstrated herein that training utilizing repeated bouts of electrical stimulation can improve bladder voiding and this effect can be augmented by additionally using physical training and/or neuromodulatory drugs in addition to eth electrical stimulation. In certain embodiments the physical training can provide postural, locomotor and/or reaching and grasping patterns in the subject. In certain embodiments the physical training can provide load bearing activities, postural/positional changes and/or sitting, and/or standing, and/or stepping activities.

In certain embodiments the physical training involves resistance training. In certain embodiments the training can involve the aid of assistive walkers and/or robotic devices or systems including, but not limited to an exoskeletal system and any robotic prosthetic device on extremity or trunk.

Use of Neuromodulatory Agents.

In certain embodiments, the transcutaneous and/or epidural stimulation methods described herein are used in conjunction with various pharmacological agents, particularly pharmacological agents that have neuromodulatory activity (e.g., are monoaminergic). In certain embodiments, the use of various serotonergic, and/or dopaminergic, and/or noradrenergic and/or GABAergic, and/or glycinergic drugs is contemplated. These agents can be used in conjunction with epidural stimulation and/or transcutaneous stimulation and/or physical training, e.g. as described above. This combined approach can help to put the spinal cord (e.g., the lumbosacral spinal cord) in an optimal physiological state for controlling voiding of the bladder.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists. Illustrative pharmacological agents include, but are not limited to agonists and antagonists to one or more combinations of serotonergic: 5-HT1A, 5-HT2A, 5-HT3, and 5HT7 receptors; to noradrenergic alpha 1 and 2 receptors; and to dopaminergic D1 and D2 receptors (see, e.g., Table 1).

TABLE 1

Illustrative pharmacological agents.

| Name | Target | Action | Route | Typical Dose (mg/Kg) | Typical Range (mg/kg) |
| --- | --- | --- | --- | --- | --- |
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |

TABLE 1-continued

Illustrative pharmacological agents.

| Name | Target | Action | Route | Typical Dose (mg/Kg) | Typical Range (mg/kg) |
| --- | --- | --- | --- | --- | --- |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

In certain embodiments the subject is administered buspirone, and/or quipazine, and/or strychnine.

Systems for Bladder Control.

In various embodiments systems for controlling and/or improving bladder function in a mammal are provided. In certain embodiments the systems comprise one or more transcutaneous electrode(s) and/or an epidural electrode(s) electrically coupled to an electrical stimulator configured to deliver transcutaneous electrical stimulation of the lumbosacral spinal cord through a transcutaneous electrode and/or epidural electrical stimulation of the lumbosacral spinal cord through an epidural electrode according to the methods described herein to initiate and/or regulate bladder function. In certain embodiments the system comprises an electrical stimulator coupled to an epidural electrode configured to deliver epidural stimulation as described herein. In certain embodiments the system comprises an electrical stimulator coupled to a transcutaneous electrode configured to deliver transcutaneous stimulation according to the methods described herein.

In certain embodiments the systems described herein further comprise an electronic device that records/monitors bladder filling. Using the information the bladder can be prevented from overfilling and/or from emptying inappropriately and bladder contraction can be administered when desired.

Sensors for monitoring bladder filling are described, for example, by Chew et al. (2013) Sci. Translat. Med., 5(210): 210ra155. Chew et al. describe an electronic device that can accurately record bladder filling from sensory nerves after spinal cord injury in rat. The device provides a design for a nerve-electrode interface that combines features of both sieve and cuff designs by confining axons in 100 μm diameter microchannels. The microchannels greatly increase extracellular resistance, thus amplifying recordable voltage potential. Inclusion of guard/reference electrodes at the ends of the microchannels suppresses noise interference. The device was developed into an implantable neuroprosthetic device with encapsulated electrodes to record cutaneous and bladder activity dorsal roots.

The device permits recording action potential firing that accurately encodes bladder filling. The device had multiple microchannels for concurrent recording, greatly improving the resolution. Using information produced by this device, bladder emptying can be artificially stimulated on demand by electrically modulating nerve firing using the methods described herein.

In certain embodiments the system(s) further include one or more training device(s) configured to assist with physical training of the subject. Illustrative training devices include, but are not limited to a treadmill, a walker, an exoskeleton, a weight machine, an exoskeleton, and an robotic training device.

The foregoing devices, systems, and methods are intended to be illustrative and non-limiting. Using the teachings provided herein, other methods involving transcutaneous electrical stimulation and/or epidural electrical stimulation and/or the use of neuromodulatory agents to improve bladder control will be available to one of skill in the art.

EXAMPLES

The following examples are offered to illustrate, but not to limit the claimed invention.

Example 1

Regulation of Autonomic Control of Bladder Voiding after a Complete Spinal Cord Injury This example demonstrates functionally overlapping sensorimotor networks controlling bladder and locomotion in a behaving, completely paralyzed rat, the activity-dependent functional plasticity of these networks, and a means of functionally separating the networks controlling micturition and locomotion with frequency-specific stimulation parameters.

Given the anatomical overlap in the neural networks within the lumbosacral spinal cord that control bladder function (de Groat et al. (1990) *J. Autonom. Nervous Syst.* 30: 71-77; de Groat and Yoshimura (2010) *Neuro. & Urodynam.*, 29, 63-76) and locomotor function (Grinner and Zangger (1979) *Exp. Brain Res.* 34: 241-261; Barbeau and Rossignol (1987) *Brain Res.* 412: 84-95; Edgerton et al. (2001) *J. Physiol.* 533: 15-22), interactive effects of bladder function and locomotion are possible. For example, de Groat et al. (de Groat and Yoshimura (2010) *Neuro. & Urodynam.*, 29, 63-76) reported that the role of afferents originating in the bladder and EUS projecting to the lumbosacral region of the spinal cord was altered significantly after a mid-thoracic SCI. This overlap in the neural control of somatic and bladder function could represent either two separate neural circuits with some overlap or a single circuit being tuned differentially via varying frequencies of activation. The purpose of the present study was, inter alia, to assess the acute and chronic effects of varying frequencies of electrical enabling motor control (eEmc) in the lumbosacral region of the spinal cord on bladder voiding after a complete, mid-thoracic spinal cord transection in adult female rats.
Results.

Interaction of Neural Networks Controlling Locomotion and Micturition

Rats with a complete mid-thoracic spinal cord transection can step bipedally on a treadmill when the upper body is supported in a harness (de Leon et al. (2002) *Brain Res, Rev.* 40: 267-273). During this body weight supported stepping, spontaneous voiding occurs intermittently with eEmc at 40 Hz between L2 and S1 and there are distinct changes in the locomotor pattern during the transition from no voiding of urine to a state where voiding is initiated (FIG. 1, panel A). Initially consistent stepping with reciprocal activation of the soleus and TA muscles is observed (non-highlighted region). Shortly prior to voiding (~2 sec in this example, red highlighted region) the pattern of stepping changes: there is a shorter step cycle, a higher amount of co-contraction between the TA and soleus, and shorter burst durations and lower iEMG levels in both muscles compared to the prior steps (FIG. 1, panels B-D). During voiding (green highlighted region), the step cycles become even shorter and the amount of co-contraction increases further. The corresponding EMG amplitude distribution plots (FIG. 1, panel B) highlight the differences in the amount of co-contraction between the soleus and TA under each condition. Reciprocal activation of the soleus and TA muscles also is observed when the rat is suspended above the treadmill (no foot contact) and the hindlimbs are air stepping when saline is infused into the bladder via a urethral catheter (FIG. 1, panel E) under the influence of 40 Hz eEmc (FIG. 1, panel F), or when pinching the tail (data not shown). The state of the spinal locomotor circuitry, however, appears to be different under each condition. For example the EMG amplitudes in the flexors and extensors are greater and the cycle periods shorter during saline infusion compared to air stepping (40 Hz) (compare FIG. 1, panels E and F).

Chronic Effects of Step Training on Bladder Voiding

Chronic step training under the influence of eEmc (40 Hz between L2 and S1) results in an increase in spontaneous bladder voiding both during routine cage activity as well as during treadmill stepping. The daily average volume of urine voided manually starting after 3 days of training (10 days post-SCI) and continuing for a period of 30 days was lower in step trained vs. untrained rats (FIG. 2), suggesting that the bladder was influenced by the additional sensory input to the spinal circuitry generated by load bearing itself.

Acute Effect of eEmc on Bladder Voiding after SCI

Figure 3:
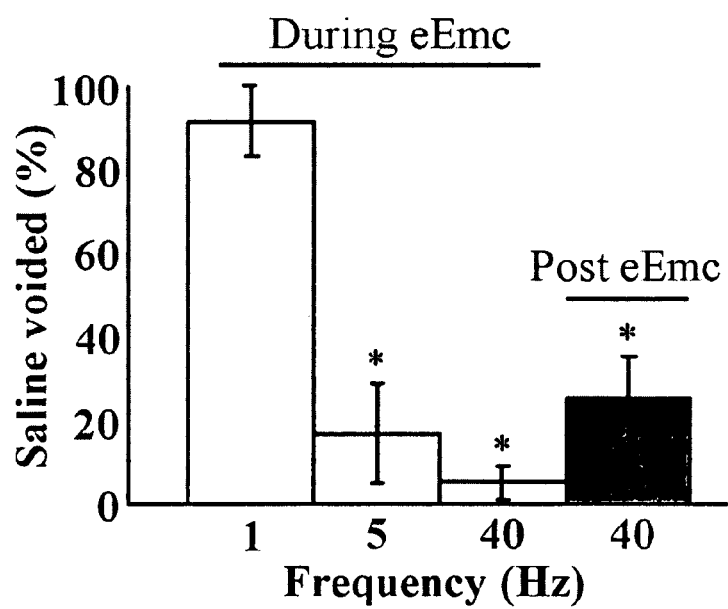
FIG. 3. Mean (±SEM, n=6 rats, 3 trials each rat) total percent volume voided in the first 90 sec after the initiation of eEmc at different frequencies after infusion of 1 cc of saline via a urethral catheter in spinal rats with the hindlimbs suspended above a treadmill belt. In addition, the volume of saline voided within 30 sec after the 40-Hz stimulation was stopped (post-eEmc) is shown. *, significantly different from 1 Hz at $P<0.05$.

We determined the effects of different frequencies of stimulation on voiding by infusing controlled quantities of saline into the bladder via a urethral catheter with step trained rats suspended in a harness as described above. One cc of saline was infused into the bladder via the urethral catheter at a steady rate since this did not result in any leakage of saline. Any volume higher than 1 cc resulted in visible leakage of saline. The most effective voiding was observed with 1-Hz stimulation, with almost 90-95% of the volume voided within 90 sec (FIG. 3). The hindlimbs show primarily a flexion motion during voiding. eEmc (40 Hz) resulted in very little voiding of saline (~5%), although a rhythmic alternating bilateral locomotor pattern of the hindlimbs was observed (FIG. 1, panel F). When stimulation at 40 Hz was stopped ~30% of the saline was voided with no movement or evoked potentials observed in the hindlimbs. With 5-Hz stimulation strong oscillatory movements in both hindlimbs were observed but only ~10-20% of the saline was voided.

Figure 4:
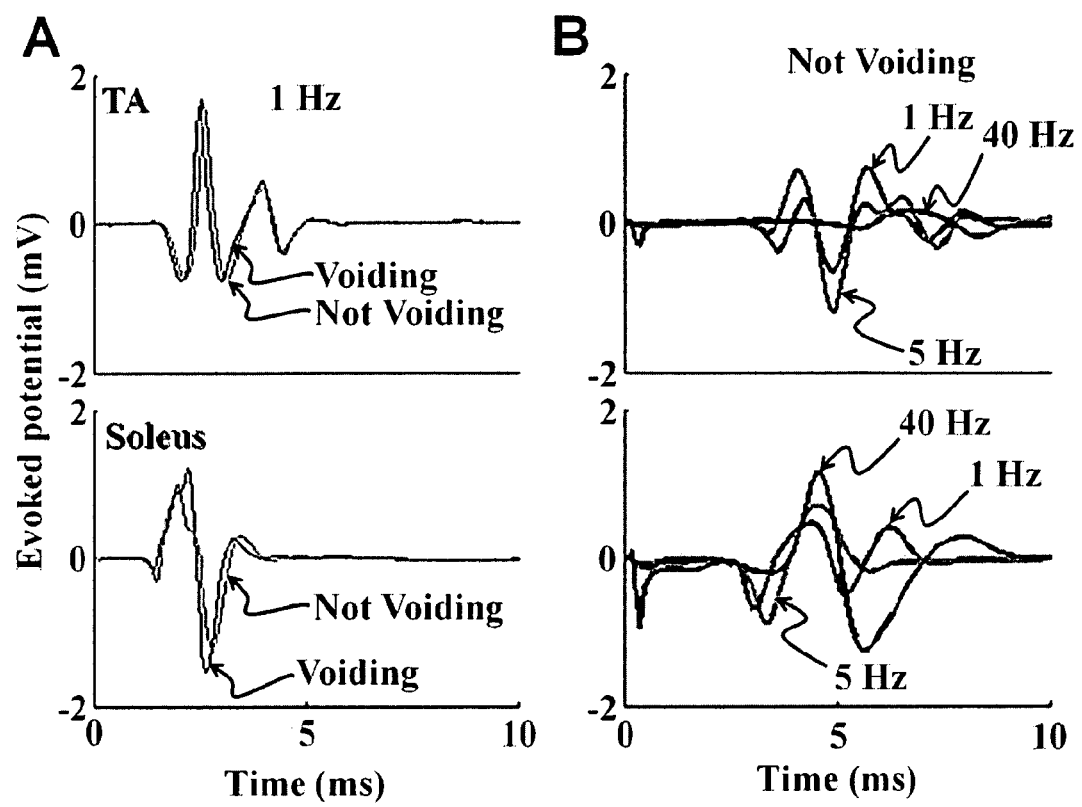
FIG. 4. Panel A: Mean evoked potentials (n=4 rats, 10 potentials for each condition/rat) from the TA and soleus muscles under the influence of eEmc at 1 Hz between L2 and S1 during voiding and not voiding with a filled bladder in a spinal rat with the hindlimbs suspended above a treadmill belt. Panel B: Mean evoked potentials (n=7 rats, 10 potentials for each condition/rat) in the soleus and TA induced by different frequencies of eEmc at 1, 5, and 40 Hz. Significant differences ($P<0.05$) in evoked potential amplitudes in the absence of voiding: TA—black<blue<red; Soleus—blue<red<black.

The responses evoked in a hindlimb extensor (soleus) and flexor (TA) muscle during 1-Hz stimulation were similar when the rats were voiding or not voiding (FIG. 4, panel A). The mean evoked responses in the TA were higher at 1 and 5 Hz vs. 40 Hz, whereas the mean amplitude of the evoked responses was progressively higher with increased stimulation frequencies in the soleus (FIG. 4, panel B). The observations of an increase in the flexor activation at the lower frequencies and of a high voiding efficiency at lower frequencies suggest a facilitatory effect of flexion on voiding.

Figure 5:
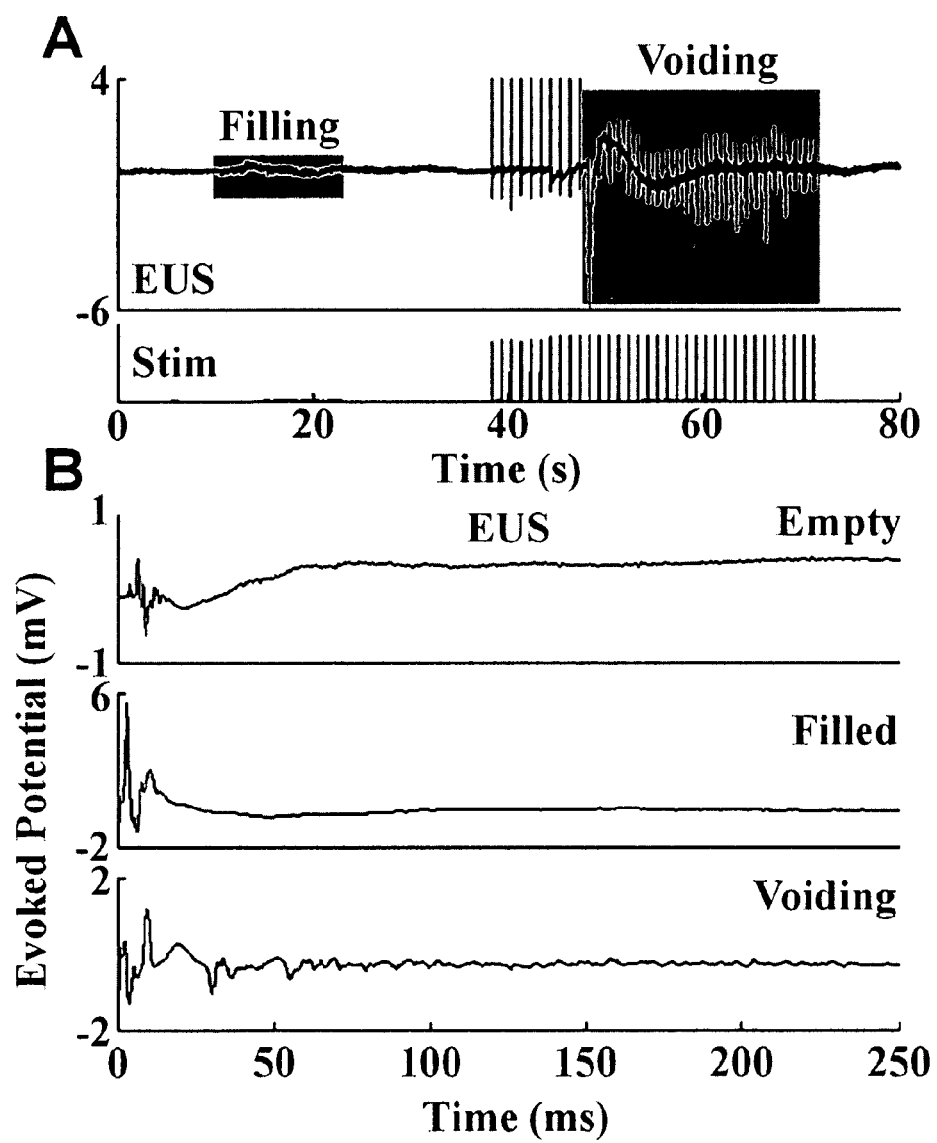
FIG. 5. Panel A: A representative EMG recording from the EUS muscle during infusion of 1 cc of saline into the bladder (orange highlight) and during voiding under the influence of 1 Hz eEmc (green highlight). Panel B: Average (20 potentials) evoked potentials recorded from the EUS muscle of a spinal rat at 1-Hz stimulation when the bladder was empty, filled, or voiding.

We then investigated the electrophysiological responses to 1-Hz stimulation after infusing saline into the bladder. Infusion of saline initially resulted in a slight increase in the activation of the EUS muscle followed by a period when the EUS was inactive (FIG. 5, panel A). Stimulation at 1 Hz increased EUS activation and bladder voiding began after about 10 sec of stimulation. The evoked potentials recorded from the EUS with the bladder empty had a low amplitude with a latency of ~3-5 ms (FIG. 5, panel B). In comparison, these responses with a filled bladder had a higher amplitude and a shorter latency than with an empty bladder. During voiding, the EUS showed two distinct peaks with the first peak having a latency similar to that with a filled bladder but with a lower amplitude and several smaller responses with latencies varying between 20-100 ms.

Figure 6:
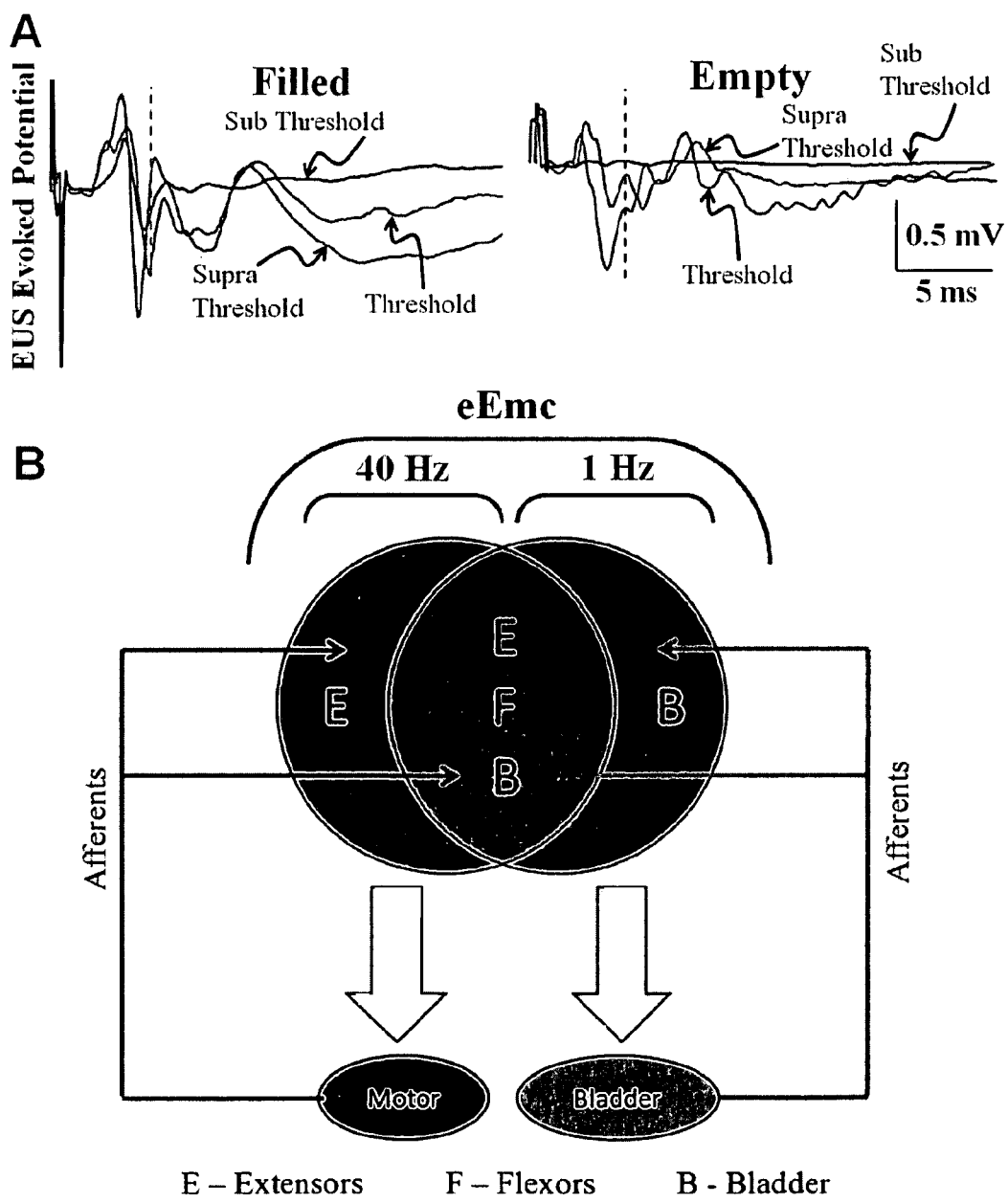
FIG. 6: Panel A: Average evoked potentials from the EUS (n=10 stimulation pulses at 1 Hz) at subthreshold, threshold, and supra-threshold intensities of stimulation (threshold was determined based on the voltage at which voiding was initiated) with a filled bladder compared to an empty bladder. Note the presence of higher amplitude evoked potentials at a sub-threshold level with a filled bladder compared to an empty bladder and higher amplitude evoked potentials at threshold compared to supra-threshold levels with a filled bladder. A similar pattern has been observed with the evoked potentials in hindlimb muscles under the same conditions (Lavrov el al. (2008) *J. Neurosci.* 28: 6022-6029). Also note the higher amplitudes and longer latencies at threshold and supra-threshold levels in a filled bladder compared to an empty bladder. Dotted line denotes the 5 ms mark. Panel B: schematic representing the overlap of the lumbosacral spinal cord circuitries controlling locomotion and bladder voiding under the influence of eEmc and afferents from the bladder and hindlimbs is shown.

Stimulation at sub-threshold levels (threshold set at voiding intensity) with a filled bladder resulted in an evoked potential in the EUS (FIG. 6, panel A, black trace). In addition, the amplitude and number of responses increased at voiding threshold and at supra-threshold levels of stimulation (FIG. 6, panel A, blue and red traces, respectively). In comparison, sub-threshold stimulation (same intensity as above) with an empty bladder did not produce an evoked potential (FIG. 6, panel A, black trace). Threshold and supra-threshold levels of stimulation, however, produced an evoked potential in the EUS, although these responses were of lower amplitude compared to those seen with a filled bladder.

Discussion.

It is well known that motor performance can be accompanied by changes of autonomic functions (somatic-visceral interactions). Recent studies of human subjects with motor complete paralysis report improvement in postural control and some voluntary movement in the legs, and the subjects anecdotally have reported improved autonomic function such as bladder, sexual, and thermoregulatory control (Harkema et al. (2011) *Lancet*, 377: 1938-1947; Angeli et al. (2014) *Brain*, 137: 1394-1409). In this study we show that enabling of locomotor-related spinal neuronal circuits by epidural stimulation also influences neural networks controlling bladder function. Herein we have demonstrated not only the long-term synergistic effects of epidural stimulation on locomotor and bladder function, but more importantly we have identified specific spinal cord stimulation parameters that initiate bladder emptying within seconds of the initiation of epidural stimulation.

Figure 2:
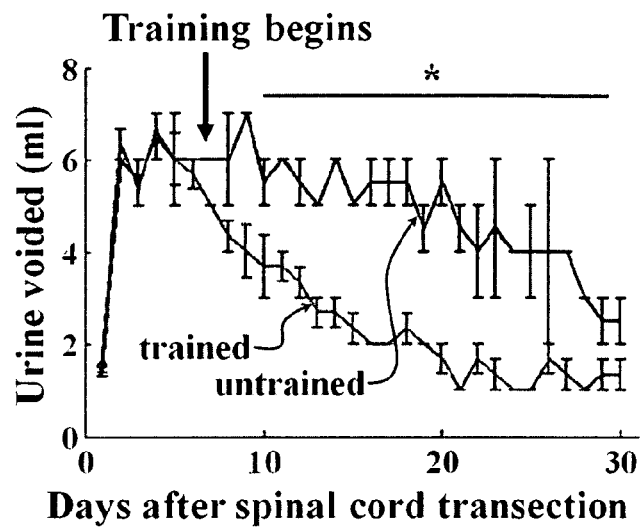
FIG. 2. Mean (±SEM) total daily volume of urine voided by manual bladder expression in spinal rats trained to step bipedally on a treadmill at 13.5 cm/s beginning 7 days post-surgery or in untrained rats (n=3 rats/group). *, significant difference between trained and untrained at $P<0.05$.

Given the locations of the neural networks within the spinal cord that control autonomic function, the level and extent of a spinal cord lesion are important factors in the extent of loss of bladder function (Potter (2006) *Progr. Brain Res.* 152: 51-57). A complete mid-thoracic spinal cord transection in rats results in the loss of bladder function initially with some autonomically initiated spontaneous control returning in the following weeks, allowing for occasional but incomplete emptying (FIG. 2). In humans with a thoracic or cervical SCI, descending projections from supraspinal centers often are severed and their axons degenerated. In many such individuals, the reflex pathways mediating continence remain intact, but micturition cannot be initiated in a normal manner (Barrington (1941) *Brain*, 64: 239-243). The most common form of this condition is detrusor-sphincter dyssynergia (de Groat et al. (1990) *J. Autonom. Nervous Syst.* 30: 71-77; de Groat and Yoshimura (2010) *Neuro. & Urodynam.* 29: 63-76) in which both the detrusor and EUS tend to be activated together rather than reciprocally.

It appears that epidural stimulation raises the net excitability level of spinal neural networks (interneurons and motoneurons) and when combined with motor training and/or pharmacological interventions, enhances the activation of the sensorimotor pathways that also control bladder function (Harkema et al. (2011) *Lancet*: 377: 1938-1947). Data presented herein demonstrate that in addition to the chronic effects, e.g., improved spontaneous bladder emptying associated with epidural stimulation and step training, we have discovered a unique spinal epidural stimulation paradigm which can overcome detrusor-sphincter dyssynergia and induce bladder emptying on demand in unanesthetized rats with a complete mid-thoracic spinal cord transection.

Spinal Cord Plasticity Mediating Locomotor and Bladder Function after a SCI

Within three days of the initiation of epidural stimulation and step training the rats started voiding spontaneously during cage activity and step training (FIG. 2). After 3 weeks of locomotor training facilitated with eEmc (40 Hz between L2 and S1) and quipazine and strychnine administration, the spinal rats consistently voided when stimulated at 1 Hz between L2 and S1. Locomotor training (Courtine et al. (2009) *Nature Neurosci.* 12: 1333-1342; Ichiyama et al. (2008) *J Neurosci.* 28: 7370-7375) with eEmc chronically engaged the neural networks by lowering the threshold of excitability and apparently when stimulated at 1 Hz the networks were tuned to initiate micturition. An underlying mechanism of the improved spontaneous control of bladder emptying is suggested by the heightened responses to the afferent-information sensing bladder volume (FIG. 6). This enhanced spontaneous voiding of the bladder was more efficient in the trained compared to untrained rats (FIG. 2), most likely reflecting the lowered activation threshold due to the chronic engagement of the neural networks in the trained rats. This result is consistent with the observation that after 8 weeks of locomotor training facilitated by epidural stimulation and pharmacological interventions the contractile responses of the bladder to filling in anesthetized spinal rats were more efficient in trained compared to untrained animals (Horst et al. (2010) *J. Pediat. Neurol.* 6: 19). Direct acute responses to epidural stimulation, however, were not reported.

Frequency Dependent Tuning of the Automaticity of the Spinal Cord

The complex functioning of bladder voiding was achieved via an eEmc tonic drive at 1 Hz between L2 and S1. The conceptual basis of selecting a given eEmc parameter was to activate the neural networks that initiate the automaticity of the coordinated contractions and relaxations of the bladder and EUS that result in bladder voiding. During stimulation at 1 Hz, the bladder contracts tonically. This response occurs in the EUS within a 20 to 100 ms time window (FIG. 5, panel B). These evoked potentials with a long latency may represent the activation of complex interneuronal networks that enable bursting activity of the EUS similar to that observed during voiding in intact rats (D'Amico and Collins (2012) *J. Neurophysiol.* 108: 2554-2567).

Stimulation at higher frequencies (40 Hz) at the same sites on the spinal cord (between L2 and 51) facilitates partial weight-bearing bipedal (Courtine et al. (2009) *Nature Neurosci.* 12: 1333-1342) and quadrupedal (Gad et al. (2012) *J. Neuroengin. Rehab.* 9: 38) stepping of spinal rats on a treadmill belt. A consistent bilateral air stepping pattern also is observed when the rats are suspended in a harness and under the influence of eEmc at 40 Hz and with sufficient levels of current (Gad et al. (2013) *J. Neurophysiol.* 110: 1311-1322) (FIG. 1, panel F). Similar bilateral air stepping-like patterns were observed in the hindlimbs during infusion of saline and tail pinching, suggesting that the afferent information from the bladder and EUS being processed by the neural networks in the lumbosacral region of the spinal cord contribute to these hindlimb responses. These results provide further evidence of an overlap between the networks controlling bladder function and locomotion.

Neural Networks Controlling Locomotion and Micturition

Over the past several decades, multiple techniques have been used to induce micturition after SCI, including stimulation of the bladder wall, the pelvic nerve, and/or the sacral nerve. Directly stimulating the bladder wall induces local contractions, but high currents or a large number of electrodes are needed to induce a more widespread contraction to achieve sufficient bladder emptying. Pelvic nerve stimulation has been shown to contract the bladder wall, but as the pelvic nerve does not innervate the EUS minimal effect was seen on the EUS resulting in a low voiding efficiency (Holmquist and Tord (1968) *Scand. J. Urol. Nephrol.* 2: 129-135). Voiding was only achieved, however, by cutting the pudendal nerve. This largely irreversible procedure eliminates sensation from the external genitalia of both sexes and the skin around the anus and perineum, as well as the motor supply to various pelvic muscles, including the external urethral sphincter and the external anal sphincter. Sacral nerve stimulation seemed to offer the best results, but requires complicated surgical procedures and a serious risk of permanent damage via the intradural approach (Rijkhoff et al. (1997) *J. Urol.,* 157: 1504-1508). Recently a closed-loop neuroprosthesis interface was used to measure bladder fullness through implanted afferent dorsal rootlets into microchannel electrodes to measure and interpret sensory activity related to bladder fullness in spinal rats (Chew et al. (2013) *Sci. Transl. Med.,* 5: 210ra155). Voiding was achieved using low frequency anterior sacral nerve stimulation. While promising, the viability of this chronically implanted dorsal root microchannel electrode system in humans has yet to be established.

Each of the above strategies involves surgically severing nerves, result in permanent loss of some motor and sensory functions, and directly induce contractions in the bladder. Therefore, these strategies completely bypass the automaticity that is intrinsic to the sensorimotor neural circuitries present in the spinal cord. While epidural electrode array implantation also is invasive, similar surgical procedures are followed in routinely performed procedures to alleviate chronic pain. Moreover, no indwelling electrodes in spinal nerves or irreversible surgical denervation of nerves or rootlets are necessary. By preserving the sensorimotor networks that underlie the automaticity of micturition, as occurs with the recovery of stepping and standing after a complete spinal cord transection, bladder function can be largely re-established by enabling the inherent automaticity present within the spinal cord (Edgerton et al. (2001) *J. Physiol.* 533: 15-22; Edgerton et al. (2004) *Ann. Rev. Neurosci.* 27: 145-167). The spinal cord circuitry contains the necessary circuitry to control bladder voiding when provided the appropriate afferent information from the bladder and the sphincter. Based on frequency-specific stimulation parameters, the spinal cord can be tuned to enable the appropriate physiological response (FIG. 6). The clinical implications of this technique are immense and parallel the impact that spinal cord stimulation has had on locomotion studies and the recovery of volitional movement after complete paralysis (Harkema et al. (2011) *Lancet,* 377: 1938-1947; Angeli et al. (2014) *Brain,* 137: 1394-1409). The application of spinal cord stimulation to overcome difficulty in micturition is not likely limited to SCI but could be adapted to other neurological disorders. This protocol could be invaluable in avoiding unnecessary transurethral catheterization, potentially lowering the incidence of urinary tract infections and reversing the uptake of urine into the kidney.

In summary, the main findings include 1) the demonstration of functional links between the neural control (biomechanical and electrophysiological) of locomotion and micturition in awake unanesthetized rats, 2) the immediate effect of in vivo spinal cord stimulation on micturition, and 3) the positive chronic effects of step training under the influence of eEmc and pharmacological interventions on bladder function.

Materials and Methods.

Study Design.

Study design Data were obtained from 15 (10 trained and 5 untrained) adult female Sprague Dawley rats (270-300 g body weight). Pre- and post-surgical animal care procedures have been described in detail previously (Roy et al. (1992) *Lab. Animal Sci.* 42: 335-343). The rats were housed individually with food and water provided ad libitum. All survival surgical procedures were conducted under aseptic conditions with the rats deeply anesthetized with isoflurane gas administered via facemask as needed. All procedures described below are in accordance with the National Institute of Health Guide for the Care and Use of Laboratory Animals and were approved by the Animal Research Committee at UCLA. All animals underwent identical surgical procedures including spinal cord transection, intramuscular EMG implantation, and spinal cord epidural electrode implantation. The rats were allowed to recover for 7 days after which step training under the influence of eEmc was initiated. Step training was performed for 6 weeks, 5 days a week for 20 min/day. At 7 weeks post-injury, the rats were tested for their ability to step bipedally on a treadmill with eEmc (40 Hz), evoked potentials were elicited using eEmc (1, 5, and 40 Hz) while suspended in a harness, and terminal bladder experiments were performed. Details of each step are given below.

Head Connector and Chronic Intramuscular EMG Electrode Implantation

A small incision was made at the midline of the skull. The muscles and fascia were retracted laterally, small grooves were made in the skull with a scalpel, and the skull was dried thoroughly. Two amphenol head connectors with Teflon-coated stainless steel wires (AS632, Cooner Wire, Chatsworth Calif.) were securely attached to the skull with screws and dental cement as described previously (Courtine et al. (2009) *Nature Neurosci.* 12: 1333-1342). Selected hindlimb muscles, i.e., the tibialis anterior (TA) and soleus, were implanted bilaterally with intramuscular EMG recording electrodes as described previously (Id.). Skin and fascial incisions were made to expose the belly of each muscle. Two wires extending from the skull-mounted connector were routed subcutaneously to each muscle. The wires were inserted into the muscle belly using a 23-gauge needle and a small notch (~0.5-1.0 mm) was removed from the insulation of each wire to expose the conductor and form the electrodes. The wires were secured in the belly of the muscle via a suture on the wire at its entrance into and exit from the muscle belly. The proper placement of the electrodes was verified during the surgery by stimulating through the head connector and post-mortem via dissection.

Spinal Cord Transection, Epidural Electrode Implantation, and Post-Surgical Animal Care Procedures A partial laminectomy was performed at the T8-T9 vertebral level to expose the spinal cord. A complete spinal cord transection to include the dura was performed at approximately the T8 spinal level using microscissors. Two surgeons verified the completeness of the transection by lifting the cut ends of the spinal cord and passing a glass probe through the lesion site. Gel foam was inserted into the gap created by the transection as a coagulant and to separate the cut ends of the spinal cord. For epidural electrode implantation, partial laminectomies were performed to expose the spinal cord at spinal levels L2 and 51. Two Teflon-coated stainless steel wires from the head connector were passed under the spinous processes and above the dura mater of the remaining vertebrae between the partial laminectomy sites. After removing a small portion (~1 mm notch) of the Teflon coating and exposing the conductor on the surface facing the spinal cord, the electrodes were sutured to the dura mater at the midline of the spinal cord above and below the electrode sites using 8.0 Ethilon suture (Ethicon, New Brunswick, N.J.). Two common ground (indifferent EMG and stimulation grounds) wires (~1 cm of the Teflon removed distally) were inserted subcutaneously in the mid-back region. All wires (for both EMG and epidural stimulation) were coiled in the back region to provide stress relief. All incision areas were irrigated liberally with warm, sterile saline. All surgical sites were closed in layers using 5.0 Vicryl (Ethicon, New Brunswick, N.J.) for all muscle and connective tissue layers and for the skin incisions in the hindlimbs and 5.0 Ethilon for the back skin incision. All closed incision sites were cleansed thoroughly with saline solution. Analgesia was provided by buprenex (0.5-1.0 mg/kg, s.c. 3 times/day). The analgesics were initiated before completion of the surgery and continued for a minimum of 2 days. The rats were allowed to fully recover from anesthesia in an incubator. The rats were housed individually in cages that had ample CareFresh bedding, and the bladders of the spinal rats were expressed manually 3 times daily for the first 2 weeks after surgery and 2 times daily thereafter. During bladder expressions, the urine was collected in a weigh boat and measured using a syringe to quantify the total urine manually expressed each day. The hindlimbs of the spinal rats were moved passively through a full range of motion once per day to maintain joint mobility. These procedures have been described in detail previously (Id.).

Step Training.

Ten rats were step trained bipedally (Ichiyama et al. (2008) *J. Neurosci.* 28: 7370-7375) on a specially designed motor-driven rodent treadmill using a body weight support system (de Leon et al. (2002) *Brain Res, Rev.* 40: 267-273) under the influence of eEmc between L2 and S1 (40 Hz) and quipazine (Ichiyama et al. (2008) *J. Neurosci.* 28: 7370-7375) (0.3 mg/kg, i.p.) and strychnine (Gad et al. (2013) *J. Neuroengineering and Rehab.* 10: 108; Gad et al. (2013) *J. Neurophysiol.* 110: 1311-1322)[13, 14] (0.5 mg/kg, i.p.) at a treadmill speed of 13.5 cm/s (Gad et al. (2013) *J. Neuroengineering and Rehab.* 10: 108). The rats were trained for a period of 6 weeks starting one week after the spinal transection surgery. Step training in spinal rats under the influence of pharmacological and/or spinal cord stimulation interventions are routine procedures that have been performed in our lab for several years (Courtine et al. (2009) *Nature Neurosci.* 12: 1333-1342; Ichiyama et al. (2008) *J Neurosci.* 28: 7370-7375; Gad et al. (2013) *J. Neuroengineering and Rehab.* 10: 108; Gad et al. (2013) *J. Neurophysiol.* 110: 1311-1322).

Testing Procedures.

All 15 rats (10 trained, 5 untrained) were tested under the following conditions: 1) the rats were tested to step bipedally at a treadmill speed of 13.5 cm/s while in a body weight support system under the influence of eEmc (40 Hz bipolar stimulation between L2 and S1); 2) evoked potentials were recorded from the hindlimb muscles during bipolar epidural stimulation between L2 and S1 (1, 5, and 40 Hz) while the rats were suspended in a harness (Ichiyama et al. (2008) *J. Neurosci.* 28: 7370-7375; Lavrov et al. (2006) *J. Neurophysiol.* 96: 1699-1710; Lavrov et al. (2008) *J. Neurosci.* 28: 6022-6029); and 3) acute terminal experiments for bladder function were performed 7 weeks post-SCI. Under anesthesia, a PE 50 catheter was inserted via the urethra (Rosas-Arellano et al. (1988) *Physiol. & Behav.* 43: 127-128) and secured in place using surgical tape. The EUS muscle was implanted acutely with Teflon coated stainless steel wires (AM systems) as described previously (D'Amico and Collins (2012) *J. Neurophysiol.* 108: 2554-2567). Once the animal was conscious, they were suspended vertically using the body weight support system with their feet off the treadmill surface (FIG. 2, panel C). One cc of saline was injected into the bladder via a syringe at a steady pace with no visible leakage of saline. Three trials were conducted at each stimulation frequency (1, 5, and 40 Hz). The saline voided during stimulation at each frequency of stimulation was collected in a large weigh boat positioned below the animal and then the volume measured using a syringe as described above. The bladder was expressed manually between each trial to ensure an empty bladder.

Data Analysis.

EMG recordings from the TA, soleus, and EUS muscles were bandpass filtered (1 Hz to 5 KHz), amplified using an A-M Systems Model 1700 differential AC amplifier (A-M Systems, Carlsborg, Wash.), and sampled at a frequency of 10 KHz using a custom data acquisition program written in the LabView development environment (National Instruments, Austin, Tex.) as described previously (Courtine et al. (2009) *Nature Neurosci.* 12: 1333-1342). Custom scripts written in Matlab were used to measure the evoked potentials from the hindlimb and EUS muscles (Gad et al. (2013) *J. Neurophysiol.* 110: 1311-1322). Step cycle durations and EMG burst durations and amplitudes were determined using a custom program written in the LabView development environment. Burst integrated EMG (iEMG) was calculated as the area under the curve after rectification of the raw EMG signal.

Statistical Analyses.

All data are reported as mean±SEM. Statistically significant differences were determined using a one-way repeated measures analysis of variance (ANOVA). The criterion level for the determination of a statistical difference was set at $P<0.05$ for all comparisons.

Example 2

Sub-Threshold Spinal Cord Stimulation Facilitates Spontaneous Motor Activity in Spinal Rats A wide range of animal spinal cord injury models and species have shown that stimulation applied to spinal neural networks can dramatically improve motor ability, i.e., enhance the ability to stand and step on a treadmill with partial body weight support (1. Iwahara et al. (1991) *Somatosens. Mot. Res.* 8:281-287; Gerasimenko et al. (2003) *Neurosci. Behav. Physiol.* 33:247-254; Ichiyama et al. (2005) *Neurosci. Lett.* 383: 339-344; Gerasimenko et al. (2008) *Exp. Neurol.* 09: 417-425; Courtine et al. (2009) *Nat. Neurosci.* 12:1333-1342; Shah et al. (2012) *Eur. J. Neurosci.* 36:2054-2062). More recently three completely paralyzed human subjects (one classified as ASIA A and two as ASIA B) were implanted with a commercially available spinal cord electrode array and stimulation package originally designed for pain suppression (Harkema et al. (2011) *Lancet*, 377: 1938-1947; Angeli et al. (2012) *SFN Abstracts* 475.26/JJ12). Epidural stimulation of specific spinal segments (via caudal electrodes at ~51 spinal level), in combination with the sensory information from the lower limbs and weeks of stand training, was sufficient to generate full weight-bearing standing. These subjects also recovered some voluntary control of movements of the toe, ankle, and the entire lower limb, but only when electrical enabling motor control (eEmc) was present. Thus, one possibility is that modulation of the excitability of the lumbosacral region of the spinal cord via eEmc, combined with the weak excitatory activity of descending axons that were not otherwise detectable, could volitionally achieve a level of excitation that was sufficient to activate the spinal motor circuits above the motor thresholds of a significant number of motoneurons among synergistic motor pools. These results in human subjects demonstrate that some patients clinically diagnosed as having complete paralysis can use proprioceptive information combined with some input from descending motor signals (perhaps residual but functionally silent without eEmc) to activate spinal motor circuits, thus generating and controlling a range of motor functions via eEmc.

There is some spontaneous activity in the paralyzed muscles after a complete mid-thoracic spinal cord transection. For example, the total amount of integrated EMG activity in the soleus and lateral gastrocnemius muscles in spinal cats during a 24-hr period was ~25% and ~33%, respectively, of that occurring in uninjured cats (Alaimo et al. (1984) *J. Appl. Physiol.* 56:1608-1613). The present experiment was designed to determine the feasibility of enhancing the amount of spontaneous cage activity of paralyzed muscles using sub-threshold intensities of stimulation via chronically implanted epidural electrodes placed over the lumbosacral spinal cord in adult spinal rats. We chose rats that had experienced a rehabilitation process to step on a treadmill for 6 weeks under the influence of eEmc because chronic step training engages and reinforces the locomotor networks that would potentially be activated during spontaneous cage activity. We determined the activity levels and movement patterns of the hindlimbs of rats having a complete spinal cord transection at a low thoracic level while in their home cages during 6-hr periods with and without continuous eEmc (40 Hz). We hypothesized that eEmc would modulate the spinal locomotor circuits such that the hindlimbs would be more active during periods with than without eEmc. This would have the effect of more frequently engaging those neural networks that control the routine, spontaneous postural and locomotor functions that are critical in defining the level of functionality after severe paralysis. In general, the results are consistent with this hypothesis.

Methods

General Animal Procedures

Data were obtained from 4 adult female Sprague Dawley rats (270-300 g body weight). Pre- and post-surgical animal care procedures have been described in detail previously (Roy et al. (1992) *Lab. Anim. Sci.* 42:335-343). The rats were housed individually with food and water provided ad libitum. All survival surgical procedures were conducted under aseptic conditions and with the rats deeply anesthetized with isoflurane gas administered via facemask as needed. All procedures described below are in accordance with the National Institute of Health Guide for the Care and Use of Laboratory Animals and were approved by the Animal Research Committee at UCLA.

Head Connector and Intramuscular EMG Electrode Implantation

A small incision was made at the midline of the skull. The muscles and fascia were retracted laterally, small grooves were made in the skull with a scalpel, and the skull was dried thoroughly. Two amphenol head connectors with Teflon-coated stainless steel wires (AS632, Cooner Wire, Chatsworth Calif.) were securely attached to the skull with screws and dental cement as described previously (Ichiyama et al. (2005) *Neurosci. Lett.* 383: 339-344; Roy et al. (1992) *Lab. Anim. Sci.* 42:335-343). Selected hindlimb muscles, i.e., the tibialis anterior (TA) and soleus (Sol), were implanted bilaterally with EMG recording electrodes as described by Roy et al. 91991) *J. Appl. Physiol.* 70:2522-2529. Skin and fascial incisions were made to expose the belly of each muscle. Two wires extending from the skull-mounted connector were routed subcutaneously to each muscle. The wires were inserted into the muscle belly using a 23-gauge needle and a small notch (~0.5-1.0 mm) was removed from the insulation of each wire to expose the conductor and form the electrodes. The wires were secured in the belly of the muscle via a suture on the wire at its entrance into and exit from the muscle belly. The proper placement of the electrodes was verified during the surgery by stimulating through the head connector and post-mortem via dissection.

Spinal Cord Transection and eEmc Electrode Implantation Procedures and Post-Surgical Animal Care A partial laminectomy was performed at the T8-T9 vertebral level. A complete spinal cord transection to include the dura was performed at approximately the T8 spinal level using microscissors. Two surgeons verified the completeness of the transection by lifting the cut ends of the spinal cord and passing a glass probe through the lesion site. Gel foam was inserted into the gap created by the transection as a coagulant and to separate the cut ends of the spinal cord.

For eEmc electrode implantation, partial laminectomies were performed to expose the spinal cord at spinal levels L2 and 51. Two Teflon-coated stainless steel wires from the head connector were passed under the spinous processes and above the dura mater of the remaining vertebrae between the partial laminectomy sites. After removing a small portion (~1 mm notch) of the Teflon coating and exposing the conductor on the surface facing the spinal cord, the electrodes were sutured to the dura mater at the midline of the spinal cord above and below the electrode sites using 8.0 Ethilon suture (Ethicon, New Brunswick, N.J.). Two common ground (indifferent EMG and stimulation grounds) wires (~1 cm of the Teflon removed distally) were inserted subcutaneously in the mid-back region. All wires (for both EMG and eEmc) were coiled in the back region to provide stress relief.

All incision areas were irrigated liberally with warm, sterile saline. All surgical sites were closed in layers using 5.0 Vicryl (Ethicon, New Brunswick, N.J.) for all muscle and connective tissue layers and for the skin incisions in the hindlimbs and 4.0 Ethilon for the back skin incision. All closed incision sites were cleansed thoroughly with saline solution. Analgesia was provided by buprenex (0.5-1.0 mg/kg, s.c. 3 times/day). The analgesics were initiated before completion of the surgery and continued for a minimum of 3 days. The rats were allowed to fully recover from anesthesia in an incubator. The rats were housed individually in cages that had ample CareFresh bedding, and the bladders of the spinal rats were expressed manually 3 times daily for the first 2 weeks after surgery and 2 times daily thereafter. The hindlimbs of the spinal rats were moved passively through a full range of motion once per day to maintain joint mobility. All of these procedures have been described in detail previously (Courtine et al. (2009) *Nat. Neurosci.* 12:1333-1342).

Stimulation and Testing Procedures

The rats went through a bipedal step training rehabilitation process (20 min a day, 5 days a week) for 6 weeks under the influence of eEmc at 40 Hz between L2 and S1 at an intensity just above threshold (Ichiyama et al. (2005) *Neurosci. Lett.* 383: 339-344) using a body weight support system (de Leon et al. (2002) *Brain Res.* 40:267-273). Chronic step training was used because it engages and reinforces the locomotor networks that would potentially be activated during spontaneous cage activity.

The rats were tested under two conditions with and without eEmc at 40 Hz between L2 and S1 at 6 weeks post-injury: 1) during bipedal stepping on a specially designed motor-driven rodent treadmill using a body weight support system (Gerasimenko et al. (2008) *Exp. Neurol.* 09: 417-425; Courtine et al. (2009) *Nat. Neurosci.* 12:1333-1342; Lavrov et al. (2006) *J. Neurosci.* 28:6022-6029; Ichiyama et al. (2008) *J. Neurosci.* 28:7370-7375); and 2) during spontaneous cage activity. The eEmc during treadmill locomotion was set just above threshold as described previously (Ichiyama et al. (2005) *Neurosci. Lett.* 383: 339-344). The threshold for eliciting a muscle twitch and corresponding time linked EMG response (soleus was used as the reference muscle) was between 1.8 to 2 V for all rats. The sub-threshold level then was set at 20% below the motor threshold, i.e., between 1.4 and 1.6 V, during the recording of spontaneous cage activity.

The spontaneous activity levels of the spinal rats were determined in their home cage. The head connector was connected via cables to a set of amplifiers and a stimulator. A swivel arrangement was attached to the cables near the head connector to allow the rats to move freely in the cage. Food (pellets, pieces of fruit, and fruit loops) was distributed throughout the cage floor to encourage movement and exploration. Video data were recorded using a camcorder with a series of IR LEDs to enable recording in the dark, i.e., the active period for the rats. EMG data were amplified and recorded using custom LabView-based data acquisition software with a sampling frequency of 10 kHz. Data were recorded for 6 continuous hours starting at 8:00 pm and ending at 2:00 am. EMG recordings from the hindlimb muscles were bandpass filtered (1 Hz to 5 KHz), amplified using an A-M Systems Model 1700 differential AC amplifier (A-M Systems, Carlsborg, Wash.), and sampled at a frequency of 10 KHz using a custom data acquisition program written in the LabView development environment (National Instruments, Austin, Tex.) as described previously (Courtine et al. (2009) *Nat. Neurosci.* 12:1333-1342).

Data Analysis

The energy in the EMG signal for both muscles was calculated by estimating the area under the curve after rectification of the raw EMG (integrated EMG) as previously described (Roy et al. (1992) *Lab. Anim. Sci.* 42:335-343; Viitasalo and Komi (1977) *Eur. J. Appl. Physiol.* 37:111-121; Whiting et al. (1984) *J. Biomech.* 17: 685-694). The amounts of integrated EMG per one-min periods of stepping and spontaneous cage activity were compared. The EMG responses during spontaneous cage activity were binned in 1-min snippets for detailed analysis. A frequency distribution was constructed by estimating the energy within each 1-min bin and joint probability distributions to show the relationship between the activity of the soleus and TA were plotted. Video data were analyzed to estimate the total amount of time that the rats were active (mobile) in their home cages during the 6-hr recording period.

Statistical Analyses

All data are reported as mean±SEM. Statistically significant differences were determined using paired t-tests. The criterion level for the determination of a statistical difference was set at $P<0.05$ for all computations.

Results.

Evidence of Enabling Vs. Inducement of Neuromuscular Activity

Figure 7:
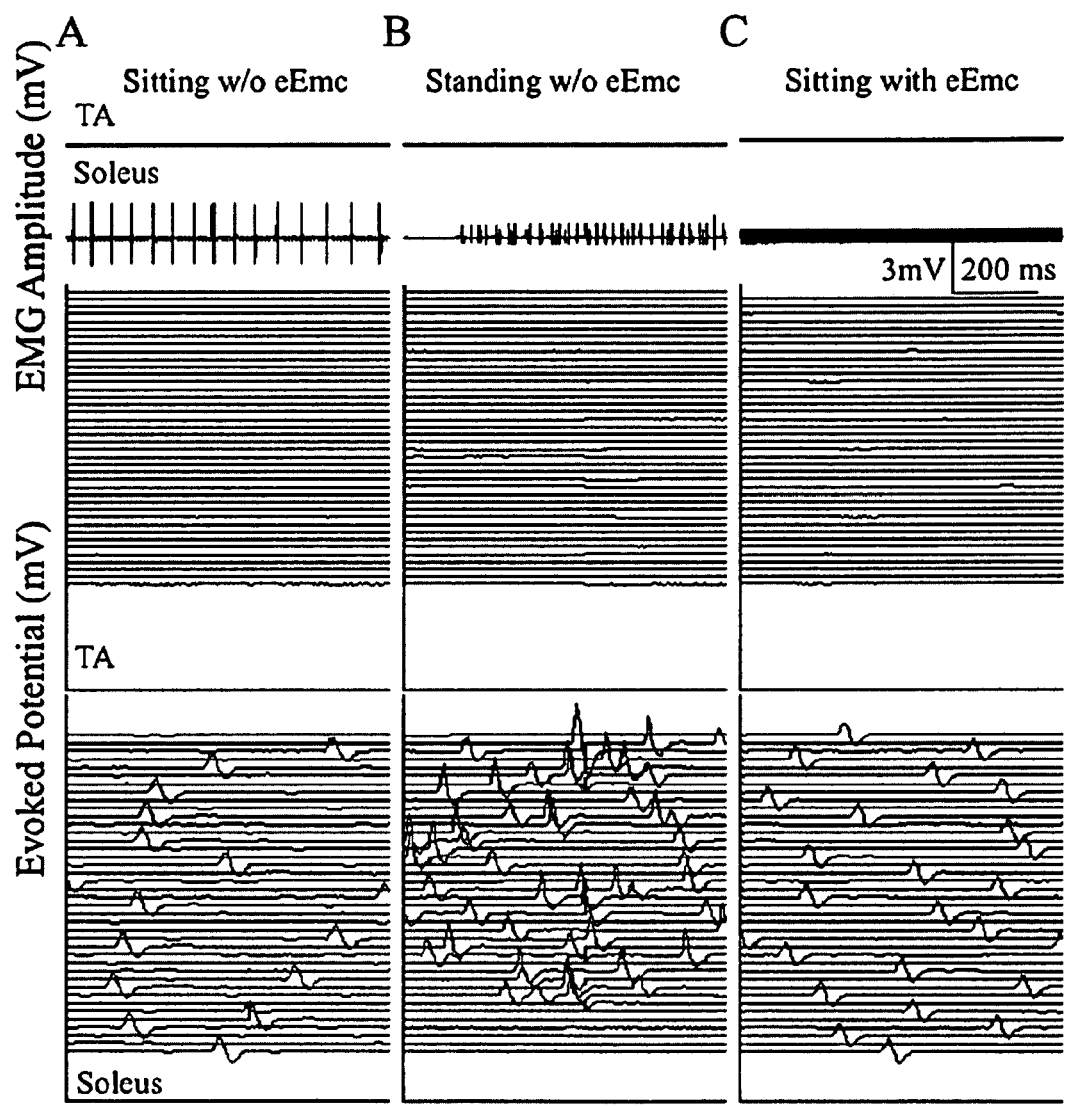
FIG. 7, panels A-F, shows representative EMG and evoked potentials with and without eEmc. Representative raw EMG and evoked potentials from the soleus and tibialis anterior (TA) muscles without eEmc from one spinal rat during (panel A) sitting, (panel B) attempted bipedal standing, and with eEmc (1.5 V, 40 Hz between L2 and S1) during (panel C) sitting, (panel D) bipedal standing, and (panel E) quadrupedal (Quad) stepping-like movement during the 6-hr recording period in its home cage. Panel F: Representative EMG and evoked potential from the soleus and TA from the same rat during body weight supported bipedal treadmill stepping facilitated by eEmc (2.0 V, 40 Hz between L2 and S1). The start of each trace with eEmc is synchronized with the initiation of the eEmc pulse. Each trace is 25 msec, i.e., the time between successive eEmc pulses. The arrow placed on the EMG signals denotes the time of the initial 25 msec scan.

We carefully examined the relationship between the absence or presence of eEmc and the amount and pattern of spontaneous cage activity. In the absence of eEmc there were periods of spontaneous activity when the rats remained in a sitting posture (FIG. 7, panel A) and on some occasions when it appeared that they were attempting to stand (FIG. 7, panel B). EMG activity increased, particularly in the soleus, during incidences of apparent attempted standing (FIG. 7, panel B). The most common observed position was for the rats to have their hindlimbs completely extended often showing little or no movement except some spastic-like reactions. Even during movement propelled by the forelimbs, the upper body remained low with the head close to the floor of the cage and the hindlimbs extended.

A sub-motor threshold intensity of eEmc is evident by the absence of any time-linked evoked muscle responses (FIG. 7, panel C). In the presence of eEmc the forelimbs were used to move around in the cage more often than in its absence. During this activity the hindlimbs usually dragged behind showing some bursting in both the flexor and extensor muscles (FIG. 7, panel E) and the upper body was maintained at a greater height compared with that seen without eEmc. The rats often would stand on the hindlimbs with partial weight bearing using the sides of the cage as support (FIG. 7, panel D), a behavior never observed without eEmc.

We compared the pattern of EMG activity during step-like movements generated spontaneously in the cage (FIG. 7, panel E) to when the rat was stepping bipedally on a treadmill using the body weight support system (FIG. 7, panel F). Note that although the stimuli imposed did not induce synchronized (time locked to stimulation pulses) motor responses with each individual stimulus (FIG. 7, panel C), it was sufficient to enable a higher level of EMG activity in the TA and soleus and to produce motor responses that were asynchronous (not time locked to stimulation pulses) as occurs in the intact state (FIG. 7, panels D and E). Also note that there is a greater level of synchronous activity during treadmill stepping (FIG. 7, panel F) than during spontaneous cage activity (FIG. 7, panel E).

Figure 8:
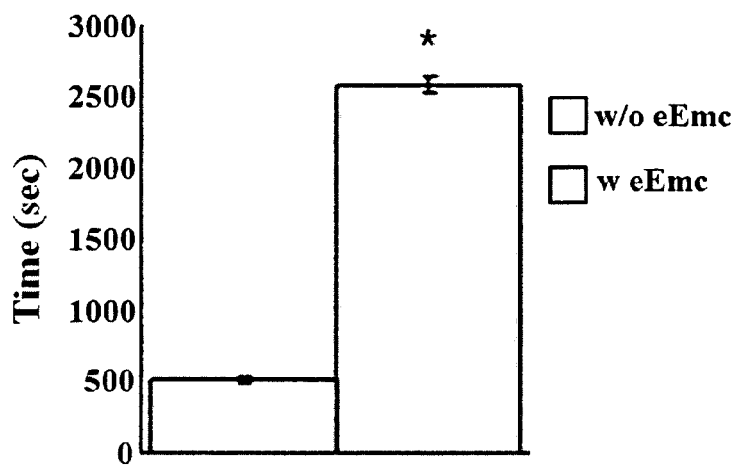
FIG. 8 shows total activity time with and without eEmc. Mean (±SEM, n=4) duration of spontaneous cage activity during the 6-hr recording period with and without eEmc at $P<0.05$.
Figure 9:
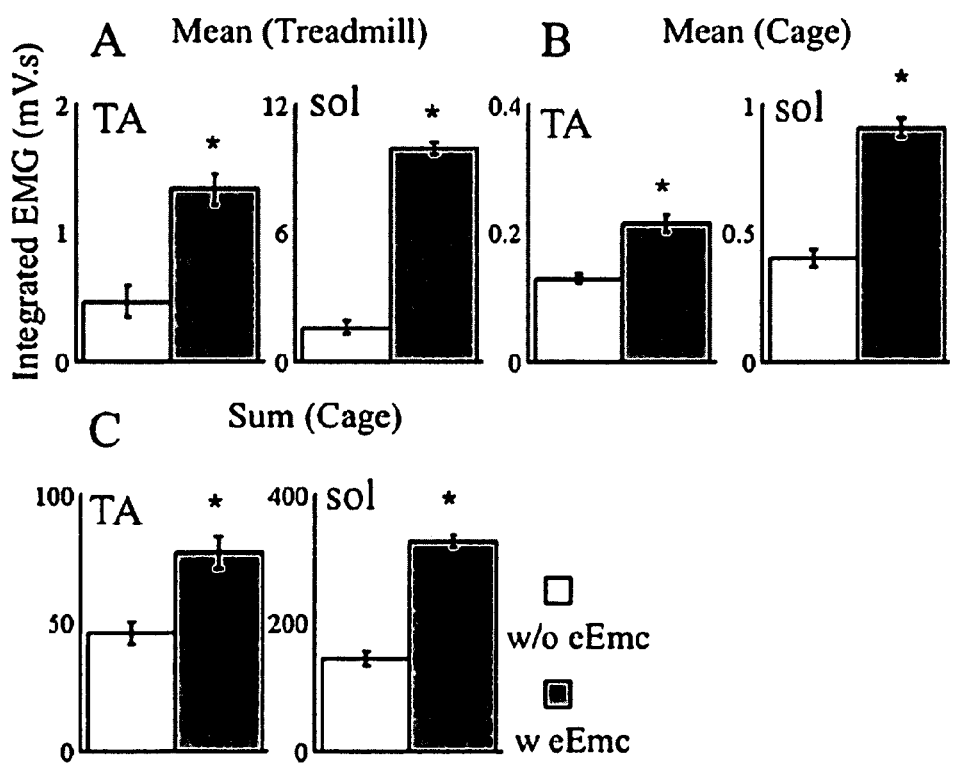
FIG. 9, panels A-C, shows integrated EMG during spontaneous cage activity and treadmill locomotion. Panel A: Integrated EMG during body weight supported treadmill stepping at 13.5 cm/sec for 1 min. Panel B: Integrated EMG per min for the TA and soleus (sol) during the 6-hr recording period in the cage. Panel C: Sum of the integrated EMG during the 6-hr recording period in the cage for the TA and soleus muscles without and with eEmc. Values are mean±SEM for 4 rats. *, significantly different from without eEmc at $P<0.05$.

The total amount of time that the rats were active during these recordings was ~5-fold higher in the presence compared to the absence of eEmc, i.e., ~2500 sec or ~12% of the time vs. ~500 sec or ~2.5% of the time (FIG. 8). The mean integrated EMG (FIG. 9, panel B) and summed integrated EMG (FIG. 9, panel C) for both the TA and soleus muscles during the 6-hr recording periods of spontaneous cage activity were significantly higher in the presence than in the absence of eEmc. To provide some point of reference regarding these increases in EMG activity with stimulation, the large differences in the mean integrated EMG in both muscles studied with and without eEmc when the rats were stepping on a treadmill are shown (FIG. 9, panel A). Furthermore, the amount of activity during the six hours of spontaneous cage activity was equivalent to ~33 minutes of stepping on the treadmill with eEmc compared to ~15 minutes without stimulation.

Figure 10:
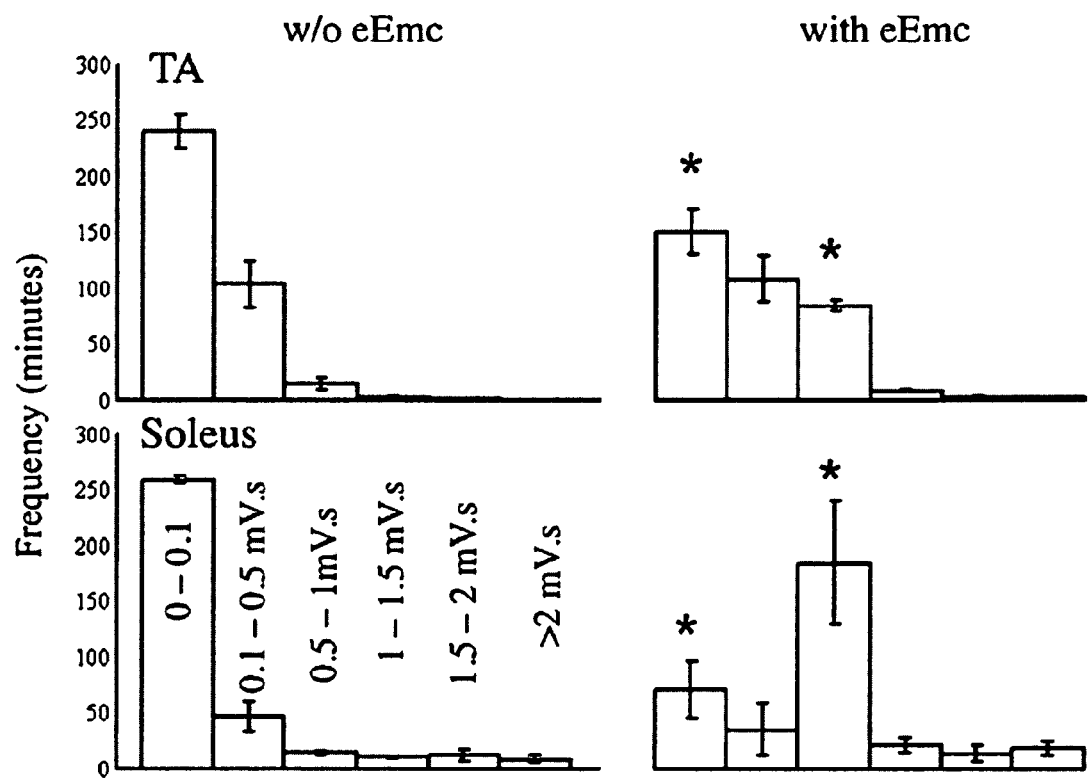
FIG. 10 shows frequency distribution of integrated EMG. Frequency distribution of the mean (±SEM, n=4 rats) integrated EMG amplitudes for the TA and soleus with and without eEmc during the 6-hr recording period in the cage expressed in one-min bins. *, significantly different from the corresponding bin without eEmc at $P<0.05$.
Figure 11:
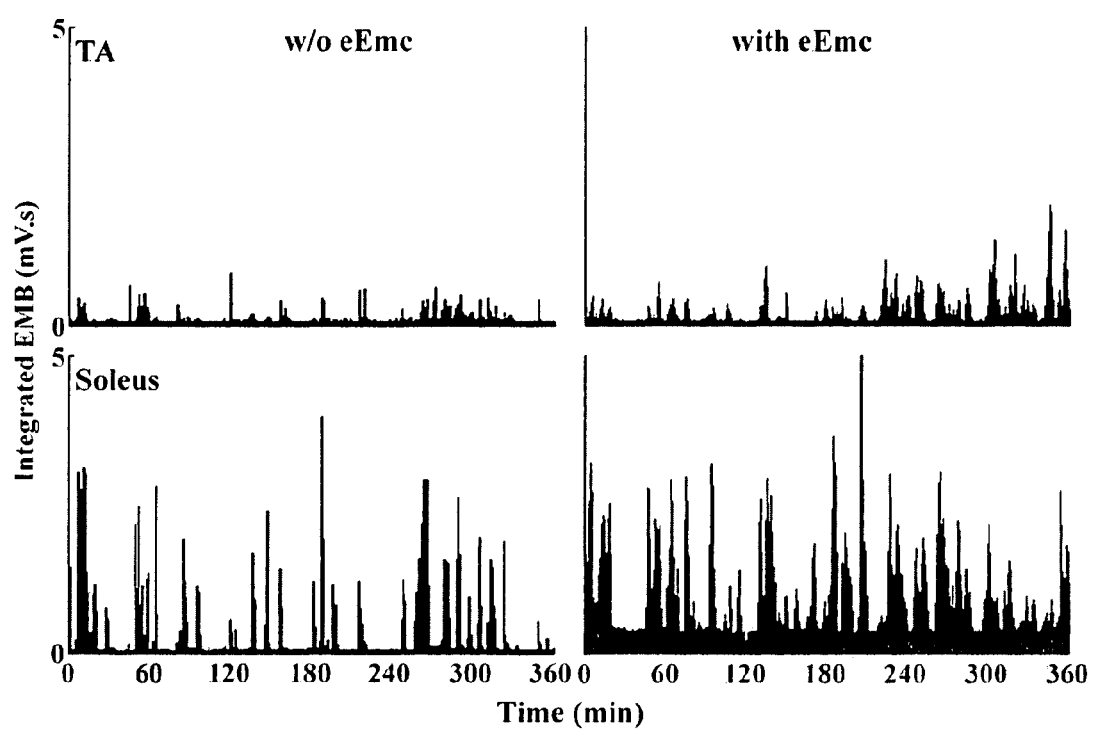
FIG. 11 shows average integrated EMG with and without eEmc. Mean (±SEM) frequency of occurrence of different ranges of integrated EMG amplitudes with and without eEmc during the 6-hr recording period of cage activity expressed in one-min bins.
Figure 12:
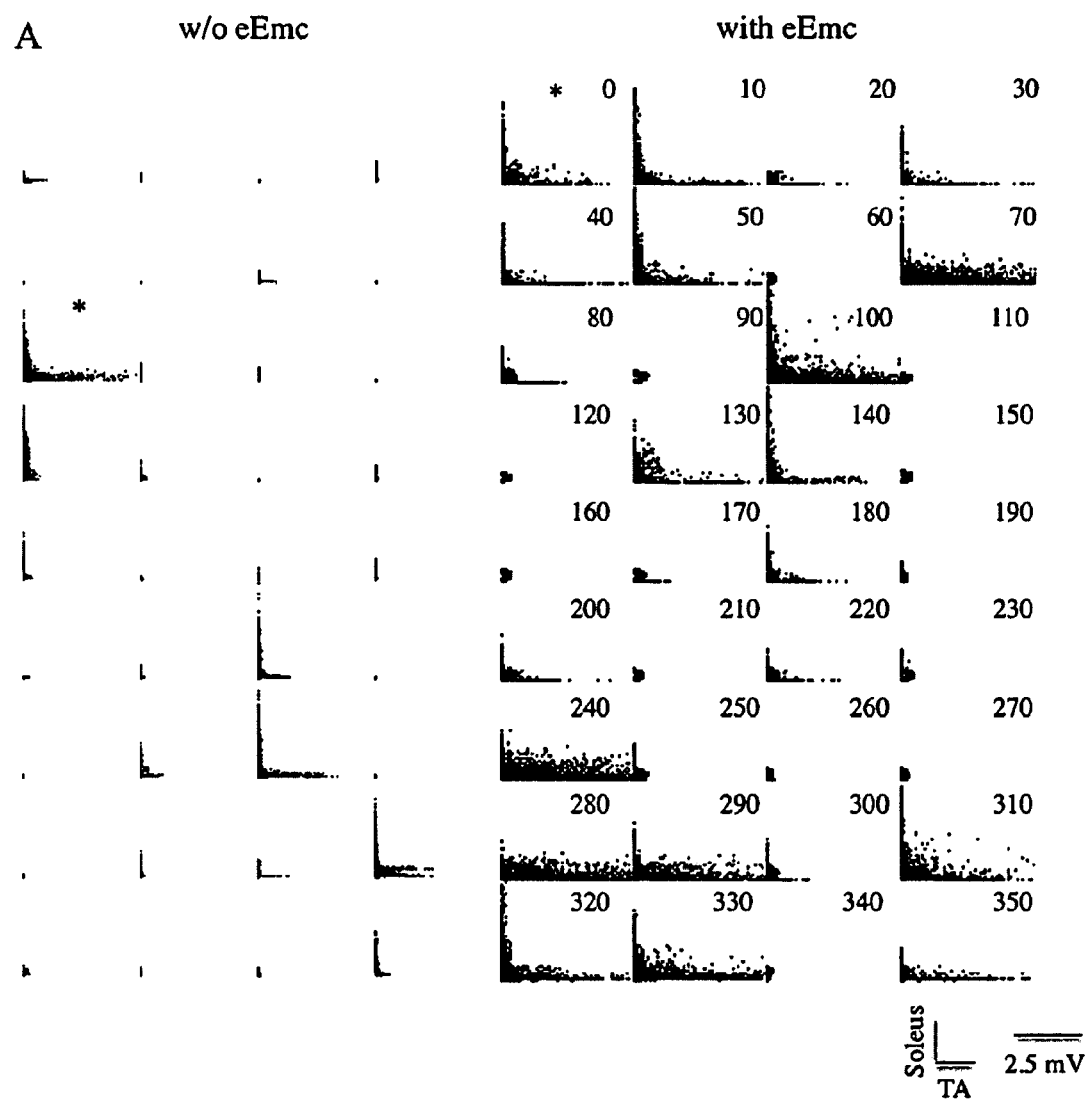
FIG. 12, panels A-B, shows JPD plots from a single animal throughout the 6 hours with and without eEmc. Panel A: Joint probability distribution plots showing the relationship between the soleus and TA activity expressed in 10-min bins during the 6-hr recording period for a representative spinal rat. The 6-hr recording occurred during the dark period (8:00 pm to 2:00 am), i.e., the active period of the rats. Panel B: The incidence of occurrence of different joint probability distributions for 10 min of activity without (I) and with (II) eEmc. The asterisks in panel A identify the two bins being compared in panel B, without eEmc (I) and with eEmc (II). Note the lack of consistent alternating flexor-extensor activation without compared to with eEmc.

There was a larger number of one-min bins with relatively high levels of integrated EMG activity with than without eEmc distributed across the 6-hr recording period for both the TA and soleus (FIG. 10). Differences in the frequency distributions of EMG amplitudes with and without eEmc also were evident (FIG. 11). Higher EMG amplitudes were observed more frequently in both the TA and soleus in the presence of eEmc. There was greater evidence of reciprocal coordination between the TA and soleus muscles with than without eEmc across the 6-hr recording period (FIG. 12, panel A). The level of EMG amplitude modulation was greater in the TA than the soleus and with this increased occurrence of higher amplitudes in the TA there was clearly a higher incidence of co-contraction between the TA and soleus muscles without eEmc. In addition, instances showing apparent reciprocal activity without eEmc had fewer and less robust alternating patterns (FIG. 12, panel B I) compared to those observed with eEmc (FIG. 12, panel B II).

DISCUSSION

Spinal circuits controlling stepping and standing after a spinal cord injury can be improved by practicing those tasks, i.e., increasing the activation of those circuits (Rosas-Arellano et al. (1988) *Physiol. & Behav.* 43: 127-128; D'Amico and Collins (2012) *J. Neurophysiol.* 108: 2554-2567). In the present study we show that there is a minimal amount of spontaneous activity in the sensorimotor circuits that can facilitate standing and stepping after a mid-thoracic spinal cord transection in adult rats. eEmc below the level of the lesion, enhanced the amount of spontaneous activity severalfold (FIG. 9 and FIG. 11) and resulted in more robust stepping-like and partial weight-bearing standing activity (FIG. 7, panels D and E). If the spontaneous activity can be enhanced with eEmc, this in effect would suggest a 'self-training' phenomenon. This effect would be consistent with the observation that independent, full weight-bearing standing can be initiated "voluntarily" and sustained in humans with complete paralysis in the presence of eEmc at an intensity that, in itself, induces little or no direct motor responses (Harkema et al. (2011) *Lancet,* 377: 1938-1947).

Does the elevated motor activity observed with subthreshold spinal cord stimulation reflect some level of "voluntary" control? The report that a completely paralyzed human subject can regain the ability to stand under the influence of eEmc (Id.) raises the question as to whether this can be considered to be "voluntarily" initiated either indirectly or via some "reflex" mechanism. There are no "reflexes" described, however, that have the motor output features performed by the paralyzed subject noted above nor the rats in the present study. While there are no widely accepted criteria for describing if a task is performed "voluntarily", the human subjects acquired the ability to initiate and sustain standing on command. Whether this could be viewed as being either a "voluntary" or an "automated" response, the subjects were able to volitionally position the upper body in a manner that increased weight bearing on the lower limbs with a critical level of eEmc. This, in turn, engaged the proprioceptive input to the spinal cord from the hindlimbs resulting in more weight-bearing activity, essentially as it seems to have been the case in the rats. To what extent can one routinely and voluntarily engage proprioception to perform a motor task? We propose that the observations in the spinal rats in the present study parallel the human data in that the rats increased their cage activity levels in the presence of sub-motor threshold stimulation intensities (FIGS. 8, 10, and 11). They were more active and mobile because the spinal networks were placed in a state of higher "readiness", making it more feasible to "volitionally" engage the postural and locomotor circuits when the rat chose to be mobile. Given that proprioception can initiate and control a wide range of postural and locomotor tasks, it seems feasible that the elevated activity in the presence of eEmc occurred as a result of the intent of the rats to be mobile as reported previously (Gad et al. (2012) *J. Neuroeng. Rehabil.* 9: 38).

The experiments in both rats (van den Brand et al. (2012) *Science,* 336: 1182-1185) and humans (Harkema et al. (2011) *Lancet,* 377: 1938-1947; Angeli et al. (2012) *SFN Abstracts* 475.26/B12) were designed to engage the "paralyzed circuits" during a specific training-rehabilitation time period in the presence of stimulation. Since the level of stimulation necessary to achieve the results noted above appeared to have little or no recognizable direct motor or behavioral effects on the animal or human subjects, we tested the hypothesis that sustained sub-threshold levels of activity in the normal cage environment would result in greater spontaneous activity among those spinal circuits that generate and control standing and stepping in rats. The implications of these observations are that the training effects induced via formal motor rehabilitation sessions could be greatly amplified during periods of routine daily activity enhanced by eEmc. These results now raise the question as to whether a general increase in activity as observed herein will result in improved standing and stepping ability compared to rats not stimulated, especially given the issue of the specificity of training. In this light, recent findings by Garcia-Alias et al. (Garcia-Alias et al. (2009) *Nat. Neurosci.* 12: 1145-1151) demonstrate that rats that are housed in an enriched environment after a spinal cord injury are more active and perform significantly better in reaching and locomotor tasks than those housed in standard cages. In addition, we have studied the effects of one stimulation paradigm and it is highly likely that other stimulation paradigms may produce more robust task-specific effects.

The spinal rats in the present study were more spontaneously active with than without eEmc, even though they were housed in standard cages. It seems likely that a combination of eEmc and an enriched housing environment would result in even greater levels of spontaneous activity, particularly in rats that are completely paralyzed. Issues related to the type and intensity of the activity performed by a spinal cord injured patient (or animal) during the prolonged daily periods without any formal rehabilitation treatment (most likely >23 hrs) have come to the forefront only recently. Even in normal humans (Finni et al. (2012) *Scand. J. Med. Sci. Sports,* doi: 10.1111/j.1600-0838.2012.01456.x) and animals (Hodgson et al. (2005) *Exp. Biol.* 208: 3761-3770) 80-90% of the daily activity occurs at very low levels of activation of almost all motor pools. With the ability to carefully quantify muscle and body activity, surprising results have been reported in how daily activity levels change when uninjured individuals begin physical training (Finni et al. (2012) *Scand. J. Med. Sci. Sports,* doi: 10.1111/j.1600-0838.2012.01456.x).

The critical questions raised now are whether the effect of epidural stimulation alone or in combination with an enriched environment would result in improved performance of reaching, standing, and locomotion and how much and what type of spontaneous activity is sufficient to enhance each of these motor tasks. Can motor performance be improved after severe paralysis by enabling the spinal circuitry during routine daily activities in the home in addition to the specific training that occurs during structured rehabilitation sessions? The spontaneous activity that may occur in a wide range of sensorimotor pathways may result in progressive improvement in specific tasks requiring fine motor control of the hands or in postural and locomotor functions, particularly if the same motor pathways are engaged as they are during scheduled rehabilitative sessions.

CONCLUSIONS

In the present study we demonstrate that that there is an enhanced amount of spontaneous activity in the sensorimotor circuits that can facilitate standing and stepping after a mid-thoracic spinal cord transection in adult rats using chronic subthreshold eEmc below the level of the lesion suggesting a novel 'self-training' phenomenon.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of improving bladder function in a subject with impaired bladder control, said method comprising:
    applying a pattern of epidural electrical stimulation or transcutaneous electrical stimulation to a lumbosacral spinal cord of said subject at a frequency and intensity that excites neural networks within said lumbosacral spinal cord sufficient to react to a second signal comprising the introduction of physical training and/or supraspinal input to induce bladder emptying and/or to improve the amount of bladder emptying.

2. The method of claim 1, wherein said subject has a spinal cord or brain injury or a neurological injury or illness.

3. The method of claim 1, wherein said electrical stimulation is at a frequency and intensity sufficient to cause at least 30% bladder emptying or to improve bladder emptying by at least 30% in response to said second signal.

4. The method of claim 1, wherein bladder emptying is initiated within 10 seconds of initiation of electrical stimulation.

5. The method of claim 1, wherein said electrical stimulation is over a region of the spinal cord comprising or consisting of the region from L1 to S5 or from L1 to S3, or from L1 to S1, or from L2 to S1.

6. The method of claim 1, wherein said electrical stimulation comprises epidural electrical stimulation of the spinal cord.

7. The method of claim 6, wherein:
    said epidural electrical stimulation of the spinal cord is at an amplitude ranging from about 0.01 mA up to about 50 mA or to about 30 mA, or from about 0.1 mA to about 20 mA, or from about 0.1 mA to about 15 mA or to about 10 mA; and/or
    said epidural electrical stimulation of the spinal cord comprises pulses having a pulse width ranging from about 1 µs to about 1 ms.

8. The method of claim 6, wherein said epidural electrical stimulation of the spinal cord is applied via a permanently implanted electrode array.

9. The method of claim 1, wherein said electrical stimulation comprises transcutaneous electrical stimulation.

10. The method of claim 9, wherein:
    said transcutaneous stimulation is at an amplitude ranging from 10 mA up to about 300 mA, or up to about 150 mA, or up to about 100 mA, or from about 20 mA to about 300 mA, or up to about 150 mA or up to about 100 mA, or from about 20 mA or from about 30 mA, or from about 40 mA up to about 50 mA, or up to about 60 mA, or up to about 70 mA or up to about 80 mA, or up to about 100 mA, or up to about 150 mA, or up to about 200 mA, or up to about 250 mA, or up to about 300 mA; and/or
    said transcutaneous stimulation pulse width ranges from about 0.5 up to about 5 ms.

11. The method of claim 9, wherein said transcutaneous electrical stimulation is superimposed on a high frequency carrier signal.

12. The method of claim 11, wherein:
    said high frequency carrier signal ranges from 3 kHz, or about 5 kHz, or about 8 kHz up to about 80 kHz, or up to about 50 kHz, or up to about 40 kHz, or up to about 30 kHz, or up to about 20 kHz, or up to about 15 kHz; and/or
    said high frequency carrier amplitude ranges up to about 300 mA.

13. The method of claim 1, wherein:
    said method does not comprise direct stimulation of the pelvic nerve; and/or
    said method does not comprise transection of the pudendal nerve; and/or
    said method does not comprise direct stimulation of the sacral nerve; and/or
    said method does not comprise direct stimulation of the anterior sacral nerve.

14. The method of claim 1, wherein said method further comprises physical training of said subject.

15. The method of claim 14, wherein:
    said physical training comprises movement of a region of the torso and/or legs of the subject; and/or
    said physical training comprises a change in postural position; and/or
    said physical training comprises a locomotor activity associated with standing and/or stepping and/or sitting; and/or
    said training comprises training against a resistance; and/or
    said training is robotically facilitated; and/or
    said training utilizes a treadmill and/or an exoskeleton, and/or a prosthesis.

16. The method of claim 1, wherein said method further comprises administration of a drug selected from the group consisting of a serotonergic drug, a dopaminergic drug, a noradrenergic drug, a GABAergic drug, and a glycinergic drug.

17. The method of claim 16, wherein said drug is selected from the group consisting of 8-hydroxy-2-(di-n-propylamino)tetralin (8-OH-DPAT), 4-(benzodioxan-5-yl)-1-(indan-2-yl)piperazine (S15535), N-{2-[4-(2-methoxyphenyl)-1-piperazinyl]ethyl}-N-(2-pyridinyl) cyclohexanecarboxamide (WAY 100.635), quipazine, strychnine, ketanserin, 4-amino-(6-chloro-2-pyridyl)-1 piperidine hydrochloride (SR 57227A), Ondansetron, buspirone, methoxamine, prazosin, clonidine, yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), quinpirole, and eticlopride.

18. The method of claim 2, wherein said subject has a spinal cord injury.

19. The method of claim 18, wherein said spinal cord injury is clinically classified as motor complete.

20. A method of training a subject having a spinal cord and/or brain injury, or other pathology causing bladder dysfunction to improve initiation of micturition and/or to improve the amount of bladder emptying, said method comprising:

administering to said subject repeated electrical stimulation training sessions according to claim 1.

21. A system for controlling and/or improving bladder function in a mammal, said system comprising a transcutaneous electrode and/or an epidural electrode electrically coupled to an electrical stimulator configured to deliver transcutaneous electrical stimulation of the lumbosacral spinal cord through a transcutaneous electrode and/or epidural electrical stimulation of the lumbosacral spinal cord through an epidural electrode according to the method of claim 1.

22. The method of claim 1, wherein said subject has a spinal cord injury causing paralysis and said improving bladder function comprises restoring bladder function by applying a pattern of electrical stimulation to the spinal cord of said subject.

23. The method of claim 1, wherein said subject has a spinal cord injury causing paralysis and said improving bladder function comprises enabling locomotor-related spinal neuronal circuits by epidural stimulation.

24. The method of claim 1, wherein said subject has a spinal cord injury causing paralysis and said improving bladder function comprises:

placing electrodes epidurally or transcutaneously on the dorsum of the spinal cord; and energizing the electrodes with a frequency-dependent stimulation pattern that is therapeutically effective.

25. The method of claim 1, wherein said subject has a pathology leading to poor bladder function.

26. The method of claim 1, wherein said method further comprises training utilizing repeated bouts of electrical stimulation.

* * * * *